US006046217A

United States Patent [19]

[11] Patent Number: 6,046,217
[45] Date of Patent: Apr. 4, 2000

Friesen et al.

[54] 2,3,5-TRISUBSTITUTED PYRIDINES AS INHIBITORS OF CYCLOOXYGENASE-2

[75] Inventors: Richard Friesen; Rejean Fortin; Daniel Dube; Denis Deschenes, all of Quebec, Canada

[73] Assignee: Merck Frosst Canada & Co., Kirkland, Canada

[21] Appl. No.: 09/151,626

[22] Filed: Sep. 11, 1998

Related U.S. Application Data

[60] Provisional application No. 60/058,630, Sep. 12, 1997.

[51] Int. Cl.$^7$ ......................... A61K 213/22; C07D 31/44

[52] U.S. Cl. .......................... 514/347; 514/247; 514/350; 514/351; 514/344; 514/352; 514/355; 514/357; 546/296; 546/297; 546/298; 546/301; 546/302; 546/309; 546/312; 546/339

[58] Field of Search .................................... 546/296, 297, 546/298, 301, 302, 309, 312, 339; 514/247, 349, 350, 351, 344, 352, 355, 357, 347

[56] References Cited

U.S. PATENT DOCUMENTS

| | | | |
|---|---|---|---|
| 5,480,568 | 1/1996 | Pawloski et al. | 514/252 |
| 5,593,994 | 1/1997 | Batt et al. | 546/21 |
| 5,686,470 | 11/1997 | Weier | 514/334 |
| 5,861,419 | 1/1999 | Dube et al. | 546/301 |

FOREIGN PATENT DOCUMENTS

| | | |
|---|---|---|
| WO 96/10012 | 4/1996 | WIPO . |
| WO 96/16934 | 6/1996 | WIPO . |
| WO 96/24584 | 8/1996 | WIPO . |

*Primary Examiner*—Zinna Northington Davis
*Attorney, Agent, or Firm*—Richard C. Billups; David L. Rose

[57] ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

I

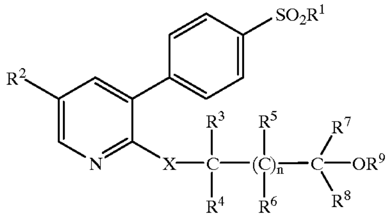

The invention also encompasses certain pharmaceutical compositions for treatment of cyclooxygenase-2 mediated diseases comprising compounds of Formula I.

17 Claims, No Drawings

2,3,5-TRISUBSTITUTED PYRIDINES AS INHIBITORS OF CYCLOOXYGENASE-2

CROSS REFERENCE TO RELATED APPLICATIONS

This application is a non provisional application related to U.S. application Ser. No. 60/058,630, filed on Sep. 12, 1997 priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

The potential utilities of selective cyclooxygenase-2 inhibitors are discussed in the following articles:

1. John Vane, "Towards a better aspirin" in *Nature*, Vol. 367, pp. 215–216, 1994
2. Bruno Battistini, Regina Botting and Y. S. Bakhle, "COX-1 and COX-2: Toward the Development of More Selective NSAIDs" in *Drug News and Perspectives*, Vol. 7, pp. 501–512, 1994.
3. David B. Reitz and Karen Seibert, "Selective Cyclooxygenase Inhibitors" in *Annual Reports in Medicinal Chemistry*, James A. Bristol, Editor, Vol. 30, pp. 179–188, 1995.
4. Don E. Griswold and Jerry L. Adams, "Constitutive Cyclooxygenase (COX-1) and Inducible Cyclooxygenase (COX-2): Rationale for Selective Inhibition and Progress to Date" in *Medicinal Research Reviews*, Vol. 16, pp. 181–206, 1996.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

I

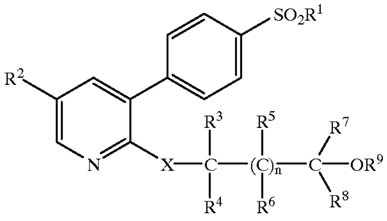

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

I

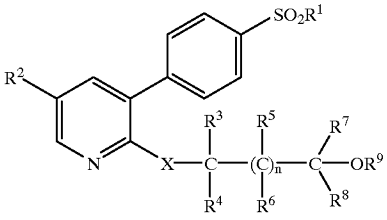

or a pharmaceutically acceptable salt thereof wherein:

X is selected from the group consisting of
- (a) O
- (b) S,
- (c) bond, n is 0 or 1, $R^1$ is selected from the group consisting of
- (a) $CH_3$,
- (b) $NH_2$,
- (c) $NHC(O)CF_3$, $R^2$ is chosen from the group consisting of
- (a) halo,
- (b) $C_{1-6}$alkoxy, (c) $C_{1-6}$alkylthio,
(d) CN,
(e) $C_{1-6}$alkyl,
(f) $C_{1-6}$fluoroalkyl,
(g) $N_3$,
(h) $—CO_2R^{10}$,
(i) hydroxy,
(j) $—C(R^{11})(R^{12})—OH$,
(k) $—C_{1-6}$alkyl-$CO_2—R^{13}$,
(l) $C_{1-6}$fluoroalkoxy,
(m) $NO_2$,
(n) $NR^{14}R^{15}$,
(o) $NHCOR^{16}$, $R^3$ to $R^{16}$ are independantly chosen from the group consisting of
(a) hydrogen
(b) $C_{1-6}$alkyl or $R^3$ and $R^7$, or $R^7$ and $R^8$ together with the atoms to which they are attached form a carbocyclic ring of 3, 4, 5, 6 or 7 atoms, or $R^3$ and $R^5$ are joined to form a bond.

One preferred embodiment of the invention is that wherein X is a bond.

Another preferred embodiment of the invention is that wherein X is O.

Another preferred embodiment of the invention is that wherein X is S.

Another preferred embodiment of the invention is that wherein $R^1$ is $CH_3$.

Another preferred embodiment of the invention is that wherein $R^2$ is halo or $C_{1-6}$fluoroalkyl.

In another aspect, the invention also encompasses a pharmaceutical composition for treating an inflammatory disease susceptable to treatment with an non-steroidal anti-inflammatory agent comprising:

a non-toxic therapeutically effective amount of a compound of formula I and a pharmaceutically acceptable carrier.

In another aspect the invention also encompasses a pharmaceutical composition for treating cyclooxygenase mediated diseases advantageously treated by an active agent that selectively inhibits COX-2 in preference to COX-1 comprising: a non-toxic therapeutically effective amount of a compound of formula I and a pharmaceutically acceptable carrier.

In another aspect the invention also encompasses a method of treating an inflammatory disease susceptable to treatment with an non-steroidal anti-inflammatory agent comprising: administration to a patient in need of such treatment of a non-toxic therapeutically effective amount of a compound of formula I and a pharmaceutically acceptable carrier.

In another aspect the invention also encompasses a method of treating cyclooxygenase mediated diseases advantageously treated by an active agent that selectively inhibits COX-2 in preference to COX-1 comprising: administration to a patient in need of such treatment of a non-toxic therapeutically effective amount of a compound of formula I.

In another aspect the invention also encompasses the use of a compound of formula I or a pharmaceutical composition in the manufacture of a medicament for the treatment of an inflammatory disease susceptable to treatment with an a non-steroidal anti-inflammatory agent.

The invention is illustrated by the compounds of the Examples disclosed herein as well as the compounds of Table I.

1) Definitions

The following abbreviations have the indicated meanings:

AA=arachidonic acid
Ac=acetyl
AIBN=2.2-azobisisobutyronitrile
Bn=benzyl
CHO=chinese hamster ovary
CMC=1-cyclohexyl-3-(2-morpholinoethyl) carbodiimidemetho-p-toluenesulfonate
COX=cyclooxygenase
DBU diazabicyclo[5.4.0]undec-7-ene
DMAP=4-(dimethylamino)pyridine
DMF=N,N-dimethylformamide
DMSO=dimethyl sulfoxide $Et_3N$=triethylamine
HBSS=Hanks balanced salt solution
HEPES=N-[2-Hydroxyethyl]piperazine-$N^1$-[2-ethanesulfonic acid]
HWB=human whole blood
IPA=isopropyl alcohol
KHMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
Mso=methanesulfonate=mesylate
NBS=N-bromosuccinimide
NCS=N-chlorosuccinimide
NIS=N-iodosuccinimide
NMO=N-methylmorpholine N-oxide
NSAID=non-steroidal anti-inflammatory drug
ODCB=o-dichlorobenzene
Oxone®=potassium peroxymonosulfate
PCC=pyridinium chlorochromate
PDC=pyridinium dichromate
r.t.=room temperature
rac.=racemic
TBAF=tetra-n-butylammonium fluoride
Tf=trifluoromethanesulfonyl=triflyl
TFAA=trifluoroacetic anhydride
TfO=trifluoromethanesulfonate=triflate
THF=tetrahydrofuran
TLC=thin layer chromatography
TMPD=N,N,N',N'-tetramethyl-p-phenylenediamine
Ts=p-toluenesulfonyl=tosyl
TsO=p-toluenesulfonate=tosylate
Tz=1H (or 2H)-tetrazol-5-yl
$SO_2Me$=methyl sulfone (also $SO_2CH_3$)
$SO_2NH_2$=sulfonamide

| Alkyl group abbreviations | | | Dose Abbreviations |
|---|---|---|---|
| Me | = | methyl | bid = bis in die = twice daily |
| Et | = | ethyl | qid = quater in die = four times a day |
| n-Pr | = | normal propyl | tid = ter in die = three times a day |

-continued

| Alkyl group abbreviations | | | Dose Abbreviations |
|---|---|---|---|
| i-Pr | = | isopropyl | |
| n-Bu | = | normal butyl | |
| i-Bu | = | isobutyl | |
| s-Bu | = | secondary butyl | |
| t-Bu | = | tertiary butyl | |
| c-Pr | = | cyclopropyl | |
| c-Bu | = | cyclobutyl | |
| c-Pen | = | cyclopentyl | |
| c-Hex | = | cyclohexyl | |

For purposes of this specification "Alkyl" means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl- 4-propylnonyl, cyclopropyl, cyclopentyl, cycloheptyl, adamantyl, cyclododecylmethyl, 2-ethyl-1-bicyclo[4.4.0]decyl and the like.

For purposes of this specification "Fluoro alkyl" means alkyl groups in which one or more hydrogen is replaced by fluorine. Examples are $—CF_3$, $—CH_2CH_2F$, $—CH_2CF_3$, c-Pr-$F_5$, c-Hex-$F_{11}$ and the like.

For purposes of this specification "Alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

For purposes of this specification "Alkylthio" means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies $—SCH_2CH_2CH_3$.

For purposes of this specification "Halo" means F, Cl, Br, or I.

Exemplifying the invention are:

(1) 2-(2-Hydroxy)ethoxy-3-(4-methylsulfonyl)phenyl-5-trifluoromethylpyridine, (2) 2-(2-Methoxy)ethoxy-3-(4-methylsulfonyl)phenyl-5-trifluoromethylpyridine, (3) 2-(2-Hydroxy-1-propyloxy)-3-(4-methylsulfonyl) phenyl-5-trifluoromethylpyridine, (4) 2-(2-Hydroxy-2-methyl-1-propyloxy)-3-(4-methylsulfonyl)phenyl-5-trifluoromethylpyridine, (5) 5-Chloro-2-(2-hydroxy-2-methyl-1-propyloxy)-3-(4-methylsulfonyl)phenylpyridine, (6) 2-(2-Methoxy-2-methyl-1-propyloxy)-3-(4-methylsulfonyl)phenyl-5-trifluoromethylpyridine, (7) 2-(2-Hydroxy-2-methyl-1-butyloxy)-3-(4-methylsulfonyl)phenyl-5-trifluoromethylpyridine, (8) 2-(2-Hydroxy-2-ethyl-1-butyloxy)-3-(4-methylsulfonyl) phenyl-5-trifluoromethylpyridine, (9) 5-Chloro-2-(2-hydroxy-2-ethyl-1-butyloxy)-3-(4-methylsulfonyl)phenylpyridine,

(10) 2-(2-Hydroxy-2-phenyl-1-propyloxy)-3-(4-methylsulfonyl)phenyl-5-trifluoromethylpyridine,

(11) 2-(1-Hydroxycyclopropyl)methoxy-3-(4-methylsulfonyl)phenyl-5-trifluoromethylpyridine,

(12) 2-(1-Hydroxycyclobutyl)methoxy-3-(4-methylsulfonyl)phenyl-5-trifluoromethylpyridine,

(13) 2-(1-Hydroxycyclopentyl)methoxy-3-(4-methylsulfonyl)phenyl-5-trifluoromethylpyridine,

(14) 5-Chloro-2-(1-hydroxycyclopentyl)methoxy-3-(4-methylsulfonyl)phenylpyridine,

(15) 2-(1-Hydroxycyclohexyl)methoxy-3-(4-methylsulfonyl)phenyl-5-trifluoromethylpyridine,

(16) 2-((2S)-3-Hydroxy-3-methyl-2-butyloxy)-3-(4-methylsulfonyl)phenyl-5-trifluoromethylpyridine,

(17) 2-((2R)-3-Hydroxy-3-methyl-2-butyloxy)-3-(4-methylsulfonyl)phenyl-5-trifluoromethylpyridine,

(18) 5-Chloro-2-((2R)-3-Hydroxy-3-methyl-2-butyloxy)-3-(4-methylsulfonyl)phenylpyridine,

(19) 2-(4-Hydroxy-4-methyl-3-pentyloxy)-3-(4-methylsulfonyl)phenyl-5-trifluoromethylpyridine,

(20) 2-((2S)-3-Ethyl-3-hydroxy-2-pentyloxy)-3-(4-methylsulfonyl)phenyl-5-trifluoromethylpyridine,

(21) 2-((2R)-3-Ethyl-3-hydroxy-2-pentyloxy)-3-(4-methylsulfonyl)phenyl-5-trifluoromethylpyridine,

(22) 2-(1-(1-Hydroxycyclopentyl)ethoxy)-3-(4-methylsulfonyl)phenyl-5-trifluoromethylpyridine,

(23) 2-((2R,3R)-3-Hydroxy-2-butyloxy)-3-(4-methylsulfonyl)phenyl-5-trifluoromethylpyridine,

(24) 5-Chloro-2-((2R,3R)-3-hydroxy-2-butyloxy)-3-(4-methylsulfonyl)phenylpyridine,

(25) 2-((2R,3S)-3-Hydroxy-2-butyloxy)-3-(4-methylsulfonyl)phenyl-5-trifluoromethylpyridrine,

(26) 2-((2S,3S)-3-Hydroxy-2-butyloxy)-3-(4-methylsulfonyl)phenyl-5-trifluoromethylpyridrine,

(27) 2-((2S,3R)-3-Hydroxy-2-butyloxy)-3-(4-methylsulfonyl)phenyl-5-trifluoromethylpyridine,

(28) 2-((2R)-1-Hydroxy-2-propyloxy)-3-(4-methylsulfonyl) phenyl-5-trifluoromethylpyridine,

(29) 2-(cis-2-Hydroxycyclopentyloxy)-3-(4-methylsulfonyl)phenyl-5-trifluoromethylpyridine,

(30) 2-(trans-2-Hydroxycyclopentyloxy)-3-(4-methylsulfonyl)phenyl-5-trifluoromethylpyridine,

(31) (+)-2-(cis-2-Hydroxy-2-methylcyclopentyloxy)-3-(4-methylsulfonyl)phenyl-5-trifluoromethylpyridine,

(32) (−)-2-(cis-2-Hydroxy-2-methylcyclopentyloxy)-3-(4-methylsulfonyl)phenyl-5-trifluoromethylpyridine,

(33) 3-(4-aminosulfonyl)phenyl-2-(cis-2-hydroxy-2-methylcyclopentyloxy)-5-trifluoromethylpyridine,

(34) 5-Chloro-2-(cis-2-hydroxy-2-methylcyclopentyloxy)-3-(4-methylsulfonyl)phenylpyridine,

(35) 2-(trans-2-Hydroxy-2-methylcyclopentyloxy)-3-(4-methylsulfonyl)phenyl-5-trifluoromethylpyridine,

(36) 2-(cis-2-Hydroxy-2-ethylcyclopentyloxy)-3-(4-methylsulfonyl)phenyl-5-trifluoromethylpyridine,

(37) 2-(cis-2-Hydroxy-2-methylcyclohexyloxy)-3-(4-methylsulfonyl)phenyl-5-trifluoromethylpyridine,

(38) 2-((3S)-3-Hydroxy-1-butyloxy)-3-(4-methylsulfonyl) phenyl-5-trifluoromethylpyridine,

(39) 2-((3R)-3-Hydroxy-1-butyloxy)-3-(4-methylsulfonyl) phenyl-5-trifluoromethylpyridine,

(40) 2-(3-Hydroxy-3-methyl-1-butyloxy)-3-(4-methylsulfonyl)phenyl-5-trifluoromethylpyridine,

(41) 2-((2R)-4-Hydroxy-2-butyloxy)-3-(4-methylsulfonyl) phenyl-5-trifluoromethylpyridine,

(42) 2-(2-Hydroxy)thioethoxy-3-(4-methylsulfonyl)phenyl-5-trifluoromethylpyridine,

(43) 2-(2-Hydroxy-2-methyl-1-thiopropyloxy)-3-(4-methylsulfonyl)phenyl-5-trifluoromethylpyridine,

(44) 5-Chloro-2-(2-Hydroxy-2-methyl- 1-thiopropyloxy)-3-(4-methylsulfonyl)phenylpyridine,

(45) (+)-2-(2-Hydroxy-2-methyl-1-thiobutyloxy)-3-(4-methylsulfonyl)phenyl-5-trifluoromethylpyridine,

(46) (−)-2-(2-Hydroxy-2-methyl-1-thiobutyloxy)-3-(4-methylsulfonyl)phenyl-5-trifluoromethylpyridine,

(47) 2-(2-Ethyl-2-hydroxy- 1-thiobutyloxy)-3-(4-methylsulfonyl)phenyl-5-trifluoromethylpyridine,

(48) 5-Chloro-2-(2-ethyl-2-hydroxy-1-thiobutyloxy)-3-(4-methylsulfonyl)phenylpyridine,

(49) 2-(1-Hydroxycyclopentyl)thiomethoxy-3-(4-methylsulfonyl)phenyl-5-trifluoromethylpyridine,

(50) 2-(3-Hydroxy-2-thiopropyloxy)-3-(4-methylsulfonyl)phenyl-5-trifluoromethylpyridine, and

(51) 5-Chloro-2-((Z)-3-Hydroxy-3-methyl-1-butenyl)-3-(4-methylsulfonyl)phenylpyridine.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of Formula I of the present invention can be prepared according to the synthetic routes outlined in Schemes 1 to 4 and by following the methods described therein.

SCHEME 1

The 2-alkoxypyridines of Formula Ia may be prepared in a multi-step sequence from the requisite 2-aminopyridine II. Initial bromination of II with bromine in acetic acid provides the bromide III. A palladium-catalyzed coupling of III with 4-(methylthio)phenylboronic acid in the presence of a suitable base, such as sodium carbonate, provides the sulfide IV which can be oxidized using one of several oxidants, such as MMPP, oxone®, or $OsO_4$/NMO to the corresponding sulfone V. The amino pyridine V can be converted to the chloride VI by treatment of V with sodium nitrite and HCl followed by reaction with POCl3. Treatment of VI with an appropriately substituted alcohol or diol VII and a suitable base such as t-BuOK in an inert solvent such as DMF provides the 2-alkoxypyridine of Formula Ia.

Scheme 1

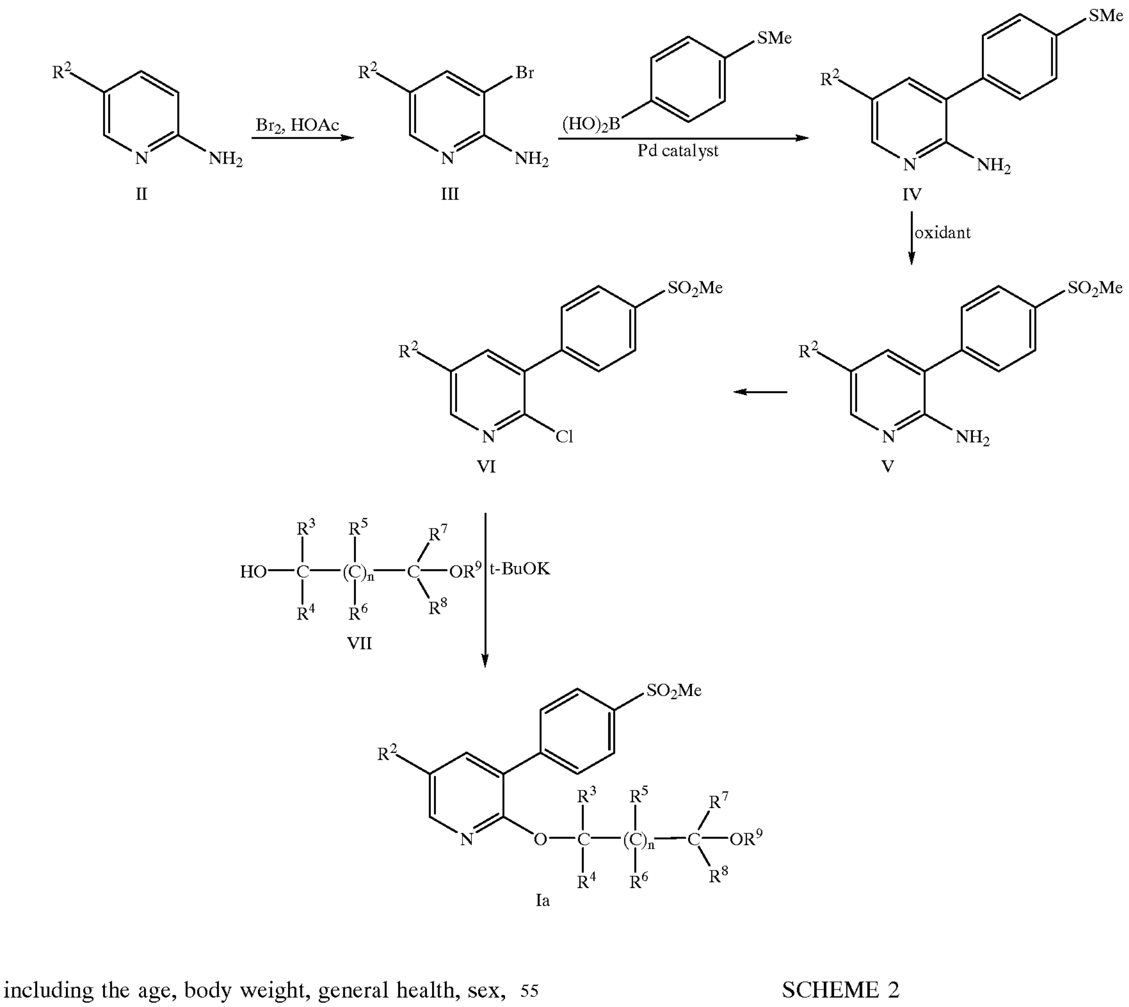

SCHEME 2

The 2-thioalkoxypyridines of Formula Ib can also be prepared from the appropriate 2-chloropyridines VI. Treatment of VI with an appropriately substituted mercaptan VIII and a base such as cesium carbonate in an inert solvent such as DMSO or DMF provides the 2-thioalkoxypyridines of Formula Ib. Alternatively, treatment of the triphenylsilylthioethers IX with a fluoride source such as TBAF in a solvent such as THF in the presence of VI also provides the 2-thioalkoxypyridines of Formula Ib.

Scheme 2

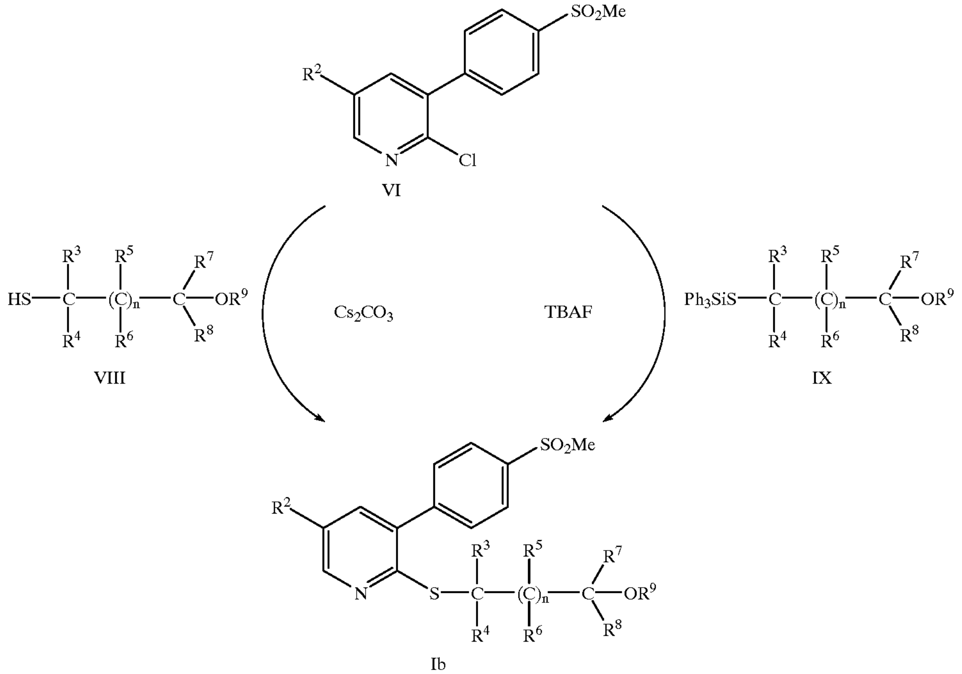

VI, VIII, IX, Ib

SCHEME 3

The aryl sulfonamides of Formula Ic can be prepared from the appropriately substituted 3-bromo-2-chloropyridines X which are obtained from the 2-amino-3-bromopyridines III by treatment with sodium nitrite and HCl followed by reaction with $POCl_3$. Treatment of X with an appropriately substituted alcohol or diol VII and a suitable base such as t-BuOK in an inert solvent such as DMF provides the 2-alkoxy-3-bromopyridine XI. A palladium-catalyzed coupling of XI with 4-(aminosulfonyl) phenylboronic acid in the presence of a suitable base, such as sodium carbonate, provides the aryl sulfonamides of Formula Ic.

Scheme 3

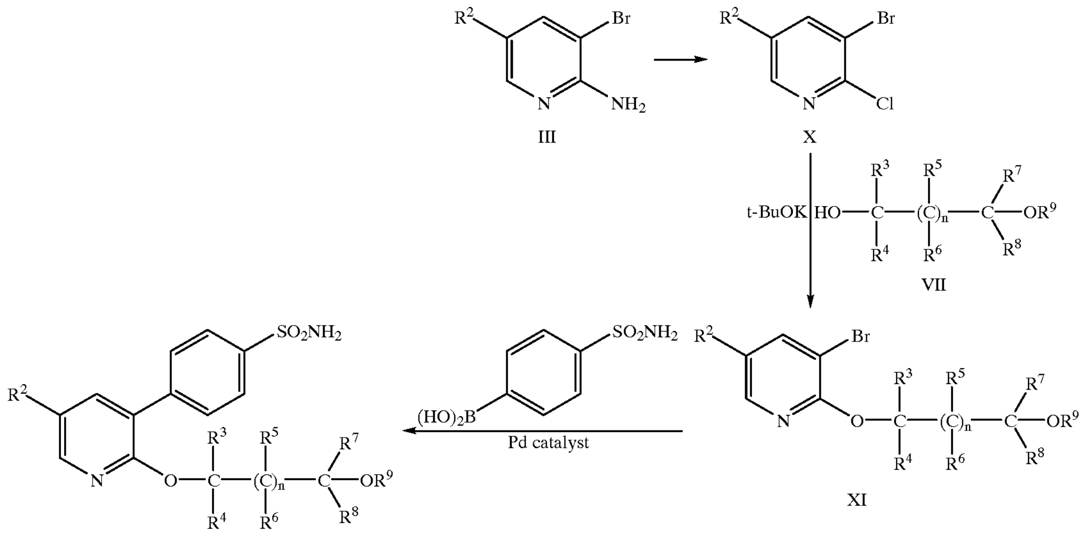

III, X, VII, XI, Ic

SCHEME 4

Additional 2-substituted pyridines of Formula Id can be obtained from the 2-chloropyridines VI. Treatment of VI with an appropriately substituted terminal acetylene XII in the presence of a palladium catalyst, such as dibromobis-triphenylphosphine palladium, a copper salt, such as CuI, and a base such as triethylamine provides 2-acetylenic pyridines XIII. Further reaction of these acetylenes provide additional examples of pyridines of Formula Id. For example, hydrogenation over a palladium catalyst, such as Lindlar's catalyst, provides the (Z)-alkenes of Formula Id.

Scheme 4

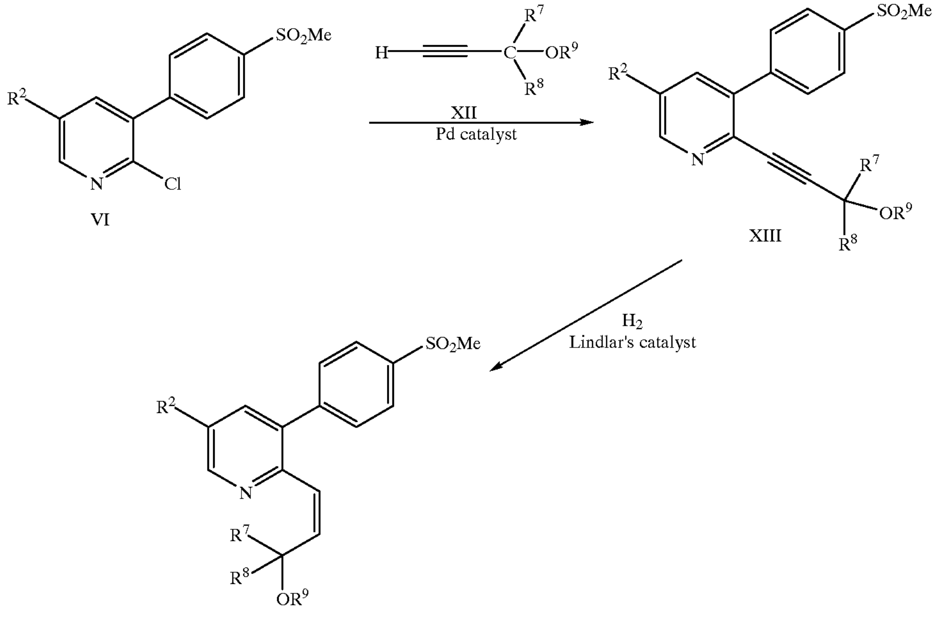

Id

Representative Compounds

Tables I illustrates novel compounds of the present invention.

TABLE I

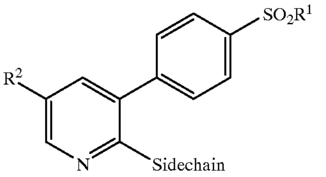

| Example | $R^1$ | $R^2$ | Sidechain | Stereochemistry |
|---|---|---|---|---|
| 1 | Me | $CF_3$ | 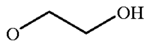 | |
| 2 | Me | $CF_3$ | 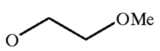 | — |
| 3 | Me | $CF_3$ | 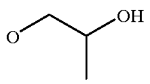 | racemic |
| 4 | Me | $CF_3$ | 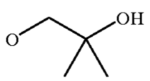 | — |

TABLE I-continued

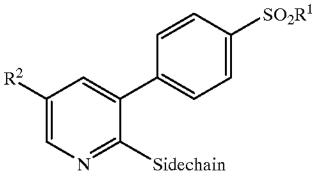

| Example | $R^1$ | $R^2$ | Sidechain | Stereochemistry |
|---|---|---|---|---|
| 5 | Me | Cl | 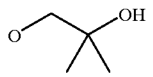 | — |
| 6 | Me | $CF_3$ | 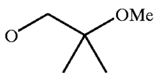 | — |
| 7 | Me | $CF_3$ | 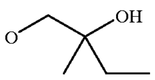 | racemic |
| 8 | Me | $CF_3$ | 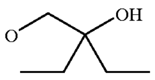 | — |

TABLE I-continued
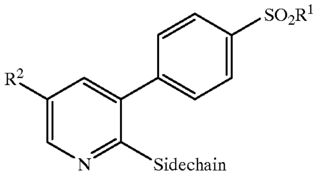
| Example | $R^1$ | $R^2$ | Sidechain | Stereochemistry |
|---|---|---|---|---|
| 9 | Me | Cl | 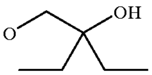 | — |
| 10 | Me | $CF_3$ | 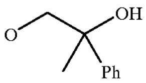 | racemic |
| 11 | Me | $CF_3$ | 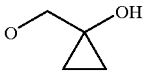 | — |
| 12 | Me | $CF_3$ | 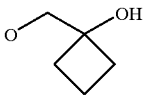 | — |
| 13 | Me | $CF_3$ | 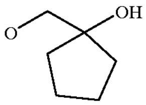 | — |
| 14 | Me | Cl | 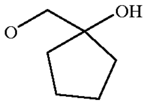 | — |
| 15 | Me | $CF_3$ | 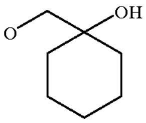 | — |
| 16 | Me | $CF_3$ | 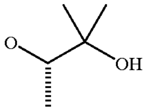 | 2S |
| 17 | Me | $CF_3$ | 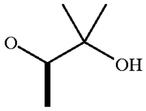 | 2R |
| 18 | Me | Cl | 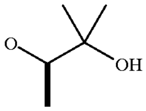 | 2R |
TABLE I-continued
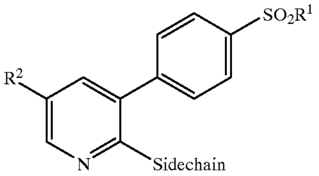
| Example | $R^1$ | $R^2$ | Sidechain | Stereochemistry |
|---|---|---|---|---|
| 19 | Me | $CF_3$ | 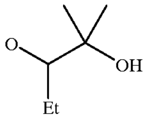 | racemic |
| 20 | Me | $CF_3$ | 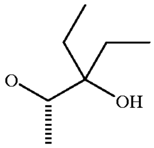 | 2S |
| 21 | Me | $CF_3$ | 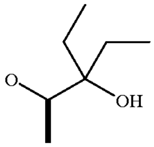 | 2R |
| 22 | Me | $CF_3$ | 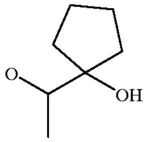 | racemic |
| 23 | Me | $CF_3$ | 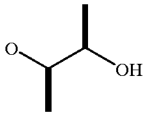 | 2R, 3R |
| 24 | Me | Cl | 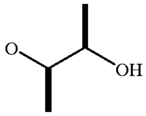 | 2R, 3R |
| 25 | Me | $CF_3$ | 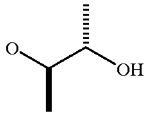 | 2R, 3S |
| 26 | Me | $CF_3$ | 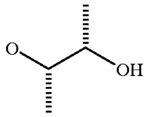 | 2S, 3S |
| 27 | Me | $CF_3$ | 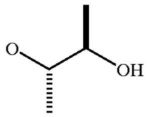 | 2S, 3R |

TABLE I-continued

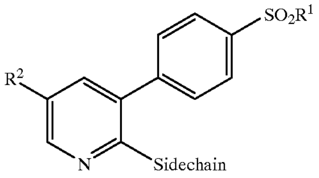

| Example | $R^1$ | $R^2$ | Sidechain | Stereochemistry |
|---|---|---|---|---|
| 28 | Me | $CF_3$ | 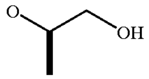 | 2R |
| 29 | Me | $CF_3$ | 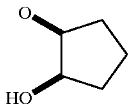 | racemic |
| 30 | Me | $CF_3$ | 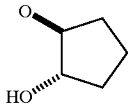 | racemic |
| 31 | Me | $CF_3$ | 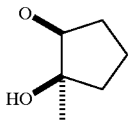 | (+)-enantiomer |
| 32 | Me | $CF_3$ | 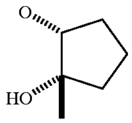 | (+)-enantiomer |
| 33 | $NH_2$ | $CF_3$ | 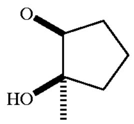 | racemic |
| 34 | Me | Cl | 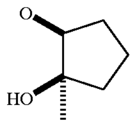 | racemic |
| 35 | Me | $CF_3$ | 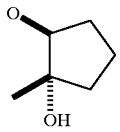 | racemic |
| 36 | Me | $CF_3$ | 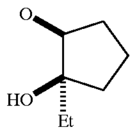 | racemic |

TABLE I-continued

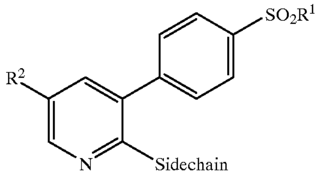

| Example | $R^1$ | $R^2$ | Sidechain | Stereochemistry |
|---|---|---|---|---|
| 37 | Me | $CF_3$ | 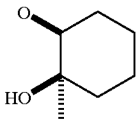 | racemic |
| 38 | Me | $CF_3$ | 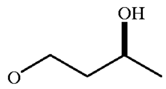 | 3S |
| 39 | Me | $CF_3$ | 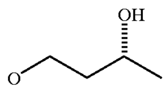 | 3R |
| 40 | Me | $CF_3$ | 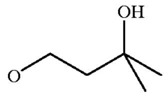 | — |
| 41 | Me | $CF_3$ | 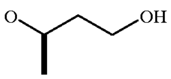 | 2R |
| 42 | Me | $CF_3$ | 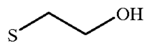 | — |
| 43 | Me | $CF_3$ | 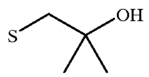 | — |
| 44 | Me | Cl | 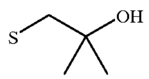 | — |
| 45 | Me | $CF_3$ | 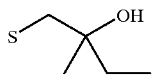 | (+)-enantiomer |
| 46 | Me | $CF_3$ | 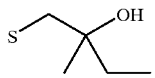 | (−)-enantiomer |
| 47 | Me | $CF_3$ | 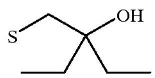 | — |
| 48 | Me | Cl | 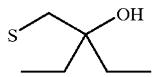 | — |
| 49 | Me | $CF_3$ | 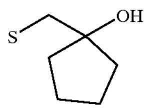 | — |

TABLE I-continued

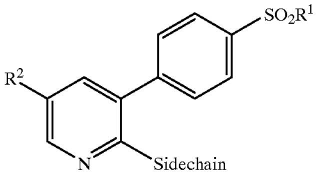

| Example | $R^1$ | $R^2$ | Sidechain | Stereochemistry |
|---|---|---|---|---|
| 50 | Me | $CF_3$ | 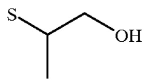 | racemic |
| 51 | Me | Cl | 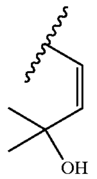 | Z-olefin |
| 52 | Me | Cl | 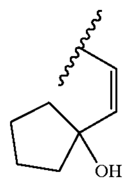 | Z-olefin |
| 53 | Me | Cl | 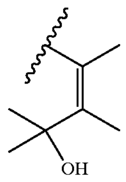 | Z-olefin |
| 54 | Me | Cl | 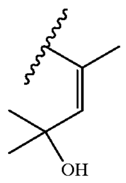 | Z-olefin |
| 55 | Me | Cl | 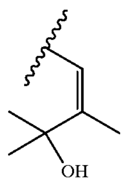 | Z-olefin |
| 56 | Me | Cl | 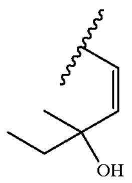 | Z-olefin, racemic |

Assays for Determining Biological Activity

The compound of Formula I can be tested using the following assays to determine their cyclooxygenase-2 inhibiting activity.

INHIBITION OF CYCLOOXYGENASE ACTIVITY

Whole cell assays for COX-2 and COX-1 using CHO transfected cell lines Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of $1.5\times10^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells ($0.3\times10^6$ cells in 200 μl) are preincubated with 3 μl of the test drug or DMSO vehicle for 15 min at 37° C. Working solutions of peroxide-free AA (5.5 μM and 110 μM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 μM AA in the CHO[hCOX-1] assay and a final concentration of 10 μM AA in the CHO[hCOX-2] assay. The reaction is terminated by the addition of 10 μl 1 N HCl followed by neutralization with 20 μl of 0.5 N NaOH. The samples are centrifuged at 300 ×g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 Cell Microsomes

U 937 cells are pelleted by centrifugation at 500×g for 5 min and washed once with phosphate-buffered saline and repelleted. Cells are resuspended in homogenization buffer consisting of 0.1 M Tris-HCl, pH 7.4, 10 mM EDTA, 2 jig/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1 M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1 M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1 M Tris-HCl buffer, pH 7.4 containing 10 mM EDTA in wells of a 96-deepwell polypropylene titre plate. 200 μl of the microsomal preparation are then added and pre-incubated for 15 min at room temperature before addition of 25 μl of 1 M arachidonic acid in 0.1 M Tris-HCl and 10 mM EDTA, pH 7.4. Samples are incubated for 40 min at room temperature and the reaction is stopped by the addition of 25 μl of 1 N HCl. Samples are neutralized with 25 μl of 1 N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the Activity of Purified Human COX-2

The enzyme activity is measured using a chromogenic assay based on the oxidation of N,N,N',N'-tetramethyl-p-phenylenediamine (TMPD) during the reduction of PGG2 to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D. /min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane B2 ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ Production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred ηL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000×g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced TxB9 Production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 ml of 1% carrageenan solution in saline (FMC Corp, Maine) into the paw using an insulin syringe with a 25-gauge needle (i.e. 500 mg carrageenan per paw). Three hr later, the paw volume ($V_3$) is measured and the increases in paw volume ($V_3$–$V_O$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

LPS-Induced Pyrexia in Conscious Rats

Male Sprague-Dawley rats (150–200 g) were fasted for 16–18 h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia. Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (*Saimiri sciureus*) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–2∞C., the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–110 g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2 ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by nonlinear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. A post hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a nonlinear least squares' regression. $ID_{50}$ was defined as the dose corresponding to a 50% reduction from the vehicle and was derived by interpolation from the fitted 4-parameter equation.

PHARMACOKINETICS IN RATS

Per Os Pharmacokinetics in Rats

PROCEDURE

- The animals are housed, fed and cared for according to the Guidelines of the Canadian Council on Animal Care.
- Male Sprague Dawley rats (325–375 g) are fasted overnight prior to each PO blood level study.
- The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum.

Water is provided at all times during the study.

Vehicles

The following vehicles may be used in PO rat blood level determinations:

PEG 200/300/400: restricted to 2 mL/kg

Methocel 0.5%–1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(\text{mg/kg})}{AUCiv}$$

The units of CL are mL/h·kg (milliliters per hour kilogram)

Intravenous Pharmacokinetics in Rats

PROCEDURE

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

Dextrose: 1 mL/kg

Moleculosol 25%: 1 mL/kg

DMSO (dimethylsulfoxide): Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(\text{mg/kg})}{AUCiv}$$

The units of CL are mL/h·kg (milliliters per hour kilogram)

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}$ Cr (5 Ci/kg in 1 ml/kg phosphate buffer saline (PBS)) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for certain of the biological assays may be seen in Table II.

TABLE II

| | COX-2 ($IC_{50}$ mM) | | COX-1 ($IC_{50}$ mM) | |
|---|---|---|---|---|
| Example | CHO | HWB | U-937 | HWB |
| 2 | 0.02 | 1.3 | 1–3 | — |
| 4 | 0.15 | 0.8 | >100 | — |
| 5 | 0.11 | 3.6 | >100 | — |
| 6 | 0.03 | <0.4 | 3–10 | — |
| 7 | 0.13 | 1.0 | >10 | — |
| 8 | 0.19 | 1.1 | >10 | — |
| 9 | 0.07 | 1.6 | >10 | — |
| 11 | 0.09 | 1.6 | 10 | — |
| 12 | 0.05 | 1.3 | >10 | — |
| 13 | 0.01 | 1.5 | 10 | 96 |
| 16 | 0.43 | 0.6 | >10 | — |
| 17 | 0.38 | <0.4 | >10 | >100 |
| 18 | 0.08 | 0.4 | >10 | — |
| 19 | 0.32 | 0.5 | >10 | — |
| 20 | 0.40 | 1.6 | >10 | — |
| 21 | 0.20 | 4.7 | >10 | >100 |
| 23 | 0.05 | 0.5 | >10 | >100 |
| 24 | 0.07 | 1.5 | >10 | — |
| 25 | 0.06 | 3.6 | >10 | — |
| 28 | 0.04 | 11.2 | >10 | >100 |
| 29 | 0.37 | 6.3 | >10 | — |
| 30 | 0.06 | 0.7 | 3–10 | — |
| 31 | 0.08 | 1.3 | 37 | >100 |
| 32 | 0.76 | 1.1 | >10 | >100 |
| 33 | 0.04 | 3.7 | 10 | — |
| 34 | 0.10 | 1.7 | >10 | — |
| 35 | — | 0.7 | 1–3 | — |
| 36 | 0.17 | 3.1 | >10 | — |
| 37 | 0.57 | 6.5 | >10 | — |
| 38 | 0.26 | 5.9 | 3–10 | — |
| 39 | 0.20 | 13.4 | >10 | — |
| 40 | 0.20 | 3.9 | 10 | — |
| 41 | 0.04 | 0.4 | >10 | — |
| 43 | 0.68 | 0.7 | 3–10 | 39 |
| 44 | 0.04 | 1.5 | >10 | — |
| 45 | 0.01 | 0.9 | 3–10 | — |
| 46 | 0.01 | 0.7 | 1–3 | — |
| 47 | 0.02 | 0.6 | 3–10 | — |
| 48 | 0.07 | 1.1 | 1–3 | — |
| 49 | 0.16 | 1.2 | 0.3 | — |
| 50 | 0.05 | 0.5 | 1–3 | — |
| 51 | 0.01 | 0.8 | 1–3 | 10 |

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)), r.t.(room temperature), h (hour(s)), min (minute(s)).

EXAMPLE 1

2-(2-Hydroxy)ethoxy-3-(4-methylsulfonyl)phenyl-5-trifluoromethylpyridine

Step 1: 2-Amino-3-bromo-5-trifluoromethylpyridine

To a solution of 2-amino-5-trifluoromethylpyridine (9 g) in acetic acid (75 mL) at r.t. was added bromine (5.8 mL) slowly. After 1 h, the acid was neutralized by the careful addition of sodium hydroxide (10 N) at 0° C. The resulting orange precipitate was dissolved in ether and washed successively with saturated potassium carbonate, saturated $Na_2SO_3$ and brine, dried and concentrated. The residual solid was stirred vigorously in hexane for 1 h to provide, after filtration, the title compound as a white solid (10.2 g).

Step 2: 2-Amino-3-(4-methylthio)phenyl-5-trifluoromethylpyridine

A mixture of the bromide from Step 1, 4-methylthiobenzene boronic acid (Li, et. al. *J. Med. Chem.* 1995, 38, 4570) (8.5 g), 2M aqueous sodium carbonate (60 mL) and palladium tetrakis(triphenylphosphine) (490 mg) in ethanol/benzene (100 mL, 1:1) was heated at reflux for 15 h. The mixture was cooled to r.t., diluted with water and extracted with ether. The organics were concentrated and the residue was subjected to stirred vigorously in ether/hexane for 1 h to provide, after filtration, the title compound (11.2 g) as a beige solid.

Step 3: 2-Amino-3-(4-methylsulfonyl)phenyl-5-trifluoromethylpyridine A mixture of 2-amino-3-(4-methylthio)phenyl-5-trifluoromethylpyridine (9.7 g), $OsO_4$ (2 mL of a 4% solution in water) and NMO (13 g) in acetone/water (60 mL:5 mL) was stirred at r.t. overnight. Saturated aqueous $Na_2SO_3$ was then added and the resulting mixture was stirred for 30 min. The acetone was evaporated and the resulting mixture was extracted with ether and ethyl acetate. The combined organics were washed with $Na_2SO_3$, water, brine and then concentrated. The solid residue was stirred vigorously in hexane and ether for 1 h and then filtered to provide the title compound as a pale yellow solid (9.9 g).

Step 4: 2-Chloro-3-(4-methylsulfonyl)phenyl-5-trifluoromethyl-pyridine

To a solution of 2-amino-3-(4-methylsulfonyl)phenyl-5-trifluoromethylpyridine (1.2 g) in water/concentrated HCl (9.5 mL:1 mL) at 0° C. was added a solution of sodium nitrite (262 mg) in 5 mL water. The mixture was warmed to r.t. and stirred overnight. An additional 30 mg of sodium nitrite was added and after 3 h the heterogeneous mixture was filtered. A portion of the solid (250 mg) and $POCl_3$ (110 mL) in DMF (2 mL) was heated at 70° C. for 60 h. The mixture was cooled to r.t., diluted with water and extracted with ethyl acetate. The organics were washed with brine, dried and concentrated to provide the title compound as a pale yellow solid (270 mg) that was used as such in the subsequent reaction.

Step 5: 2-(2-Hydroxy)ethoxy-3-(4-methylsulfonyl)phenyl-5-trifluoromethylpyridine To a solution of ethylene glycol (560 mL) in DMF (5 mL) at room temperature was added potassium t-butoxide (5 mL of a 1M solution in THF). After 5 minutes, 2-chloro-3-(4-methylsulfonyl)phenyl-5-trifluoromethylpyridine (335 mg) was added as a solid and the resulting mixture was stirred until tlc analysis indicated completion of the reaction (15 h). To the mixture was added saturated $NH_4Cl$ and the mixture was extracted with ethyl acetate. The organics were dried ($MgSO_4$) and concentrated. Flash chromatography or stirring the residual material vigorously in a suitable solvent (such as ether or ethyl acetate) provided the title compound as a white solid (250 mg), m.p. 138–139.5° C.

EXAMPLE 2

2-(2-Methoxy)ethoxy-3-(4-methylsulfonyl)phenyl-5-trifluoromethylpyridine

Following the procedures described in Example 1, but substituting 2-methoxyethanol for ethylene glycol, the title compound was obtained as a white solid.

Elemental Analysis: Calculated: C, 51.2; H, 4.3; N. 3.73 Found: C, 50.75; H, 4.31; N, 3.71

EXAMPLE 3

2-(2-Hydroxy-1-propyloxy)-3-(4-methylsulfonyl)phenyl-5-trifluoromethylpyridine

Step 1: 2-(2-Hydroxy-1-propyloxy)-3-(4-methylsulfonyl)phenyl-5-trifluoromethylpyridine and 2-(3-Hydroxy-2-propyloxy)-3-(4-methylsulfonyl)phenyl-5-trifluoromethylpyridine Following the procedures described in Example 1, but substituting 1,2-propanediol for ethylene glycol, the title compounds were obtained (520 mg) as a mixture of products after column chromatography (7:3:2 to 1:1:2 hexane/ethyl acetate/$CH_2Cl_2$) and stirring vigorously in hexane/ether.

Step 2: 3-(4-Methylsulfonyl)phenyl-2-(2-oxo-1-propyloxy)-5-trifluoromethylpyridine A mixture of the compounds from Step 1 (500 mg), PCC (850 mg) and Celite in $CH_2Cl_2$ (15 mL) was stirred at r.t. for 24 h. The mixture was poured onto a column of silica gel and eluted with ether. The eluant was concentrated and stirred vigorously in hexane/ether. The title compound was obtained as a white solid (300 mg).

Step 3: 2-(2-Hydroxy- 1-propyloxy)-3-(4-methylsulfonyl)phenyl-5-trifluoromethylpyridine To a solution of the ketone from Step 2 (130 mg) in THF/ethanol (4:1) was added NaBH4 (excess). After 15 min, saturated $NH_4Cl$ was added and the mixture extracted with ether. The organics were dried and concentrated and the residual solid was stirred vigorously in hexane/ether. The title compound was obtained as a white solid (120 mg).

Elemental Analysis: Calculated: C, 51.2; H, 4.3; N, 3.73 Found: C, 50.51; H, 4.43; N, 3.60

EXAMPLE 4

2-(2-Hydroxy-2-methyl-1-propyloxy)-3-(4-methylsulfonyl)phenyl-5-trifluoromethylpyridine Step 1: 2-Methyl-1,2-propanediol To a solution of ethyl 2-hydroxyisobutyrate (5 g) in THF (45 mL) was added lithium aluminum hydride (2.1 g). The mixture was stirred for 15 h and then sodium potassium tartarate salt solution was carefully added until a white suspension formed. The mixture was diluted with ether, filtered and the organics were concentrated. The title compound was obtained as a colorless oil that was used without further purification.

Step 2: 2-(2-Hydroxy-2-methyl-1-propyloxy)-3-(4-methylsulfonyl)phenyl-5-trifluoromethylpyridine Following the procedures described in Example 1, but substituting 2-methyl-1,2-propanediol from Step 1 for ethylene glycol, the title compound was obtained as a white solid.

Elemental Analysis: Calculated: C, 52.44; H, 4.66; N, 3.6 Found: C, 52.45; H, 4.62; N. 3.53

EXAMPLE 5

5-Chloro-2-(2-hydroxy-2-methyl-1-propyloxy)-3-(4-methylsulfonyl)phenylpyridine

Step 1: 2-Amino-3-bromo-5-chloropyridine

To a solution of 2-amino-5-chloropyridine (10 g) in acetic acid (75 mL) at r.t. was added bromine (2.6 mL) slowly. After 30 min, the acid was neutralized by the careful addition of sodium hydroxide (10 N) at 0° C. The resulting orange precipitate was dissolved in ethyl acetate and washed successively with saturated potassium carbonate, saturated $Na_2S_2O_3$ and brine, dried and concentrated. Flash chromatography (eluting with hexane/ethyl acetate, 3:1 v/v) of the residual solid provided the title compound as a pale yellow solid (14.8 g).

Step 2: 2.5-Dichloro-3-(4-methylsulfonyl)phenylpyridine

Following the procedures described in Example 1, Steps 2 to 4, but substituting 2-amino-3-bromo-5-chloropyridine from Step 1 (5 g) for 2-amino-3-bromo-5-trifluoromethylpyridine, the title compound was obtained as a white solid (5 g).

Step 3: 5-Chloro-2-(2-hydroxy-2-methyl-1-propyloxy)-3-(4-methylsulfonyl)phenylpyridine Following the procedures described in Example 4, but substituting 2,5-dichloro-3-(4-methylsulfonyl) phenylpyridine from Step 2 for 2-chloro-3-(4-methylsulfonyl)phenyl-5-trifluoromethylpyridine, the title compound was obtained as a white solid.

$^1$H NMR (300 MHz, acetone-$d_6$): d 1.22 (s, 6H), 3.17 (s, 3H), 3.73 (s, 1H), 4.21 (s, 2H), 7.90 (d, 1H), 8.00 (d, 2H), 8.02 (d, 2H), 8.20 (d, 1H).

EXAMPLE 6

2-(2-Methoxy-2-methyl-1-propyloxy)-3-(4-methylsulfonyl)phenyl-5-trifluoromethylpyridine Step 1: 2-Methoxy-2-methyl-1-propanol To a solution of isobutylene oxide (1 g) in methanol (25 mL) at −78° C. was added $BF_3 \cdot OEt_2$ (4.14 mL) and the resulting mixture was stirred at −30° C. for 24 h. The solution was neutralized with aqueous sodium bicarbonate and extracted with ethyl acetate. The organics were dried ($MgSO_4$) and concentrated. The crude material containing the title compound was used in the subsequent reaction.

Step 2: 2-(2-Methoxy-2-methyl-1-propyloxy)-3-(4-methylsulfonyl)phenyl-5-trifluoromethylpyridine Following the procedures described in Example 1, but substituting 2-methoxy-2-methyl-1-propanol from Step 1 for ethylene glycol, the title compound was obtained as a white solid.

Elemental Analysis: Calculated: C, 53.59; H, 5.0; N, 3.47 Found: C, 53.77; H, 5.37; N. 3.56

EXAMPLE 7

2-(2-Hydroxy-2-methyl-1-butyloxy)-3-(4-methylsulfonyl)phenyl-5-trifluoromethylpyridine Step 1: 2-Methyl-1,2-butanediol To ethylmagnesium bromide (18 mL of a 2.3 M solution in ether) at 0° C. was added acetol (1.5 mL) dropwise. The mixture was stirred at r.t. for 30 min and then saturated $NH_4Cl$ and saturated brine were added. The mixture was extracted with ethyl acetate and the organics were concentrated. Kugelrohr distillation of the residue provided the title compound as a colorless oil.

Step 2: 2-(2-Hydroxy-2-methyl-1-butyloxy)-3-(4-methylsulfonyl)phenyl-5-trifluoromethylpyridine Following the procedures described in Example 1, but substituting 2-methyl-1,2-butanediol from Step 1 for ethylene glycol, the title compound was obtained as a white solid.

Elemental Analysis: Calculated: C, 53.59; H, 5.0; N. 3.47 Found: C, 53.21; H, 4.97; N. 3.40

EXAMPLE 8

2-(2-Hydroxy-2-ethyl-1-butyloxy)-3-(4-methylsulfonyl)phenyl-5-trifluoromethylpyridine Step 1: 2-Ethyl-1,2-butanediol To a mixture of 2-ethyl-1-butene (2 mL) and $NMO \cdot H_2O$ (3.3 g) in THF (50 mL) was added $OsO_4$ (300 mL of a 2% solution in water). After stirring at r.t. for 15 h, saturated aqueous $Na_2S_2O_5$ was added and the resulting mixture was stirred for 30 min. Solid sodium chloride was added and the resulting mixture was extracted with ethyl acetate. The combined organics were washed with $Na_2SO_3$, brine and then concentrated. The title compound was obtained as a solid and used without further purification.

Step 2: 2-(2-Hydroxy-2-ethyl-1-butyloxy)-3-(4-methylsulfonyl)phenyl-5-trifluoromethylpyridine Following the procedures described in Example 1, but substituting 2-ethyl-1,2-butanediol from Step 1 for ethylene glycol, the title compound was obtained as a white solid.

Elemental Analysis: Calculated: C, 54.67; H, 5.31; N, 3.36 Found: C, 54.47; H, 5.19; N, 3.31

EXAMPLE 9

5-Chloro-2-(2-hydroxy-2-ethyl-1-butyloxy)-3-(4-methylsulfonyl)phenylpyridine

Following the procedures described in Example 5, but substituting 2-ethyl-1,2-butanediol from Example 8, Step 1 for 2-methyl-1,2-propanediol, the title compound was obtained as a white solid.

Elemental Analysis: Calculated: C, 56.32; H, 5.78; N, 3.65 Found: C, 54.37; H, 5.84; N, 3.71

EXAMPLE 10

2-(2-Hydroxy-2-phenyl-1-propyloxy)-3-(4-methylsulfonyl)phenyl-5-trifluoromethylpyridine Following the procedures described in Example 1, but substituting 2-phenyl-1,2-propanediol for ethylene glycol, the title compound was obtained as a white solid.

Elemental Analysis: Calculated: C, 58.53; H. 4.47; N, 3.1 Found: C, 58.43; H, 4.33; N, 3.22

EXAMPLE 11

2-(1-Hydroxycyclopropyl)methoxy-3-(4-methylsulfonyl)phenyl-5-trifluoromethylpyridine Step 1: (1-Hydroxycyclopropyl)methanol To a solution of 1-hydroxy-1-cyclopropanecarboxylic acid (1 g) in THF (10 mL) at 0° C. was added lithium aluminum hydride (15 mL of a 1 M solution in THF). The mixture was stirred for 1 h at room temperature and then 1 M sodium potassium tartarate salt solution was carefully added until a white suspension formed. The mixture was diluted with ether, filtered and the organics were concentrated. Kugelrohr distillation of the residual material provided the title compound as a colorless oil.

Step 2: 2-(1-Hydroxycvclopropyl)methoxy-3-(4-methylsulfonyl)phenyl-5-trifluoromethylpyridine Following the procedures described in Example 1, but substituting (1-hydroxycyclopropyl)methanol from Step 1 for ethylene glycol, the title compound was obtained as a white solid.

Elemental Analysis: Calculated: C, 52.71; H, 4.16; N. 3.62 Found: C, 52.51; H, 4.19; N, 3.54

EXAMPLE 12

2-(1-Hydroxycyclobutyl)methoxy-3-(4-methylsulfonyl)phenyl-5-trifluoromethylpyridine Step 1: (1-Hydroxymethyl)cyclobutanol Following the procedures described in Example 8, Step 1, but substituting methylenecylcobuatane for 2-ethyl-1-butene, the title compound was obtained as an oil and used without further purification.

Step 2: 2-(1-Hydroxycyclobutyl)methoxy-3-(4-methylsulfonyl)phenyl-5-trifluoromethylpyridine Following the procedures described in Example 1, but substituting (1-hydroxymethyl)cyclobutanol from Step 1 for ethylene glycol, the title compound was obtained as a white solid.

Elemental Analysis: Calculated: C, 53.86; H, 4.52; N, 3.49 Found: C, 53.99; H, 4.50; N, 3.48

EXAMPLE 13

2-(1-Hydroxycyclopentyl)methoxy-3-(4-methylsulfonyl)phenyl-5-trifluoromethylpyridine Step 1: (1-Hydroxymethyl)cyclopentanol Following the procedures described in Example 8, Step 1, but substituting methylenecylcopentane for 2-ethyl-1-butene, the title compound was obtained as an oil and used without further purification.

Step 2: 2-(1-Hydroxycyclopentyl)methoxy-3-(4-methylsulfonyl)phenyl-5-trifluoromethylpyridine Following the procedures described in Example 1, but substituting (1-hydroxymethyl)cyclopentanol from Step 1 for ethylene glycol, the title compound was obtained as a white solid.

Elemental Analysis: Calculated: C, 54.93; H, 4.85; N, 3.37 Found: C, 55.15; H, 4.76; N, 3.36

EXAMPLE 14

5-Chloro-2-(1-hydroxycyclopentyl)methoxy-3-(4-methylsulfonyl)phenylpyridine

Following the procedures described in Example 1, but substituting (1-hydroxymethyl)cyclopentanol from Example 13, Step 1 for ethylene glycol, the title compound was obtained as a white solid, m.p. 1122.5–113° C.

EXAMPLE 15

2-(1-Hydroxycyclohexyl)methoxy-3-(4-methylsulfonyl)phenyl-5-trifluoromethylpyridine Step 1: (1-Hydroxymethyl)cyclohexanol Following the procedures described in Example 8, Step 1, but substituting methylenecylcohexane for 2-ethyl-1-butene, the title compound was obtained as a solid and used without further purification.

Step 2: 2-(1-Hydroxycyclohexyl)methoxy-3-(4-methylsulfonyl)phenyl-5-trifluoromethylpyridine Following the procedures described in Example 1, but substituting (1-hydroxymethyl)cyclohexanol from Step 1 for ethylene glycol, the title compound was obtained as a white solid.

Elemental Analysis: Calculated: C, 55.94; H, 5.16; N, 3.26 Found: C, 56.20; H, 5.33; N, 3.21

EXAMPLE 16

2-((2S)-3-Hydroxy-3-methyl-2-butyloxy)-3-(4-methylsulfonyl)phenyl-5-trifluoromethylpyridine Step 1: (S)-Methyl 2-(3-(4-methylsulfonyl)phenyl-5-trifluoromethylpyridinyl-2-oxy)propanoate Following the procedures described in Example 1, but substituting (S)-methyl lactate for ethylene glycol, the title compound was obtained as a white solid.

Step 2: 2-((2S)-3-Hydroxy-3-methyl-2-butyloxy)-3-(4-methylsulfonyl)phenyl-5-trifluoromethylpyridine To a solution of the ester from Step 1 (230 mg) in THF (6 mL) at r.t was added methyl magnesium bromide (800 mL of a 3 M solution in ether). After 1 h, saturated $NH_4Cl$ was added and the mixture extracted with ether. The organics were dried and concentrated. Flash chromatography of the residual material (3:2 hexane/ethyl acetate) provided the title compound as a white solid.

Elemental Analysis: Calculated: C, 53.59; H, 5.0; N, 3.47 Found: C, 53.29; H, 4.93; N, 3.37

EXAMPLE 17

2-((2R)-3-Hydroxy-3-methyl-2-butyloxy)-3-(4-methylsulfonyl)phenyl-5-trifluoromethylpyridine Step 1: (2R)-3-Methyl-2,3-butanediol To methyl magnesium chloride (8 mL of a 3 M solution in THF) at r.t was added a solution of (R)-methyl lactate (500 mg) in THF (1 mL). The mixture was refluxed for 30 min and then saturated $NH_4Cl$ was added and the mixture extracted with ethyl acetate. The organics were concentrated and the residual material, containing the title compound, was used without further purification in the next reaction. Step 2: 2-((2R)-3-Hydroxy-3-methyl-2-butyloxy)-3-(4-methylsulfonyl)phenyl-5-trifluoromethylpyridine Following the procedures described in Example 1, but substituting (2R)-3-methyl-2,3-butanediol from Step 1 for ethylene glycol, the title compound was obtained as a white solid, m.p. 129–130° C.

EXAMPLE 18

5-Chloro-2-((2R)-3-Hydroxy-3-methyl-2-butyloxy)-3-(4-methylsulfonyl)phenylpyridine Following the procedures described in Example 17, but substituting 2,5-dichloro-3-(4-methylsulfonyl)phenylpyridine from Example 5, Step 2 for 2-chloro-3-(4-methylsulfonyl)phenyl-5-trifluoromethylpyridine, the title compound was obtained as a white solid.

$^1H$ NMR (300 MHz, acetone-$d_6$): d 1.15 (s, 3H), 1.16 (s, 3H), 1.28 (d, 3H), 3.16 (s, 3H), 3.52 (s, 1H), 5.21 (q, 1H), 7.86 (d, 1H), 7.96 (d, 2H), 7.99 (d, 8.18 (d, 1H).

EXAMPLE 19

2-(4-Hydroxy-4-methyl-3-pentyloxy)-3-(4-methylsulfonyl)phenyl-5-trifluoromethylpyridine Step 1: 2-Methyl-2,3-pentanediol To methyl magnesium bromide (10 mL of a 3 M solution in ether) at r.t. was added a solution of methyl 3-hydroxybutyrate (600 mg) in THF (10 mL). After 1 h, saturated NH4Cl was added and the mixture extracted with ether. The organics were dried and concentrated. Flash chromatography of the residual material (7:3 hexane/ethyl acetate) provided the title compound as an oil.

Step 2: 2-(4-Hydroxy-4-methyl-3-pentyloxy)-3-(4-methylsulfonyl)phenyl-5-trifluoromethylpyridine Following the procedures described in Example 1, but substituting 2-methyl-2,3-pentanediol from Step 1 for ethylene glycol, the title compound was obtained as a white solid.

Elemental Analysis: Calculated: C, 54.67; H, 5.31; N, 3.36 Found: C, 54.40; H, 5.45; N, 3.27

EXAMPLE 20

2-((2S)-3-Ethyl-3-hydroxy-2-pentyloxy)-3-(4-methylsulfonyl)phenyl-5-trifluoromethylpyridine Step 1: (2S)-3-Ethyl-2,3-pentanediol Following the procedures described in Example 17, but substituting (S)-methyl lactate for (R)-methyl lactate and ethyl magnesium bromide for methyl magnesium chloride, the title compound was obtained as an oil that was used without further purification.

Step 2: 2-((2S)-3-Ethyl-3-hydroxy-2-pentyloxy)-3-(4-methylsulfonyl)phenyl-5-trifluoromethylpyridine Following the procedures described in Example 1, but substituting (2S)-3-ethyl-2,3-pentanediol from Step 1 for ethylene glycol, the title compound was obtained as a white solid, m.p. 90-91° C.

EXAMPLE 21

2-((2R)-3-Ethyl-3-hydroxy-2-pentyloxy)-3-(4-methylsulfonyl)phenyl1-5-trifluoromethylpyridine Following the procedures described in Example 17, but substituting ethyl magnesium bromide for methyl magnesium chloride, the title compound was obtained as a white solid, m.p. 87–89° C.

EXAMPLE 22

2-(1-(1-Hydroxycyclopentyl)ethoxy)-3-(4-methylsulfonyl)phenyl-5-trifluoromethylpyridine Step 1: 1-(1-Hydroxyethyl)-cyclopentanol To sodium hydride (1.16 g washed with pentane) was added DMSO (42 mL) and the mixture was heated carefully to 80° C. After 45 min, the mixture was cooled to 0° C. and triphenylphosphoniumethyl bromide (11.3 g) in DMSO (30 mL) was added. The mixture was stirred at r.t. for 10 min and then cyclopentanone (2.45 mL) was added. After 30 min, ethylenecyclopentane was distilled from the reaction mixture. Dihydroxylation of this alkene was accomplished following the procedures described in Example 8, Step 1, to provide the title compound as an oil that was used as such without further purification.

Step 2: 2-(1-(1-Hydroxycyclopentyl)ethoxy)-3-(4-methylsulfonyl)phenyl-5-trifluoromethylpyridine Following the procedures described in Example 1, but substituting 1-(1-hydroxyethyl)-cyclopentanol from Step 1 for ethylene glycol, the title compound was obtained as a white solid, m.p. 100–100.5° C.

EXAMPLE 23

2-((2R,3R)-3-Hydroxy-2-butyloxy)-3-(4-methylsulfonyl)phenyl-5-trifluoromethylpyridine Following the procedures described in Example 1, but substituting (2R,3R)-2,3-butanediol for ethylene glycol, the title compound was obtained as a white solid.

Elemental Analysis: Calculated: C, 52.44; H, 4.66; N, 3.6 Found: C, 52.34; H. 4.51; N. 3.54

EXAMPLE 24

5-Chloro-2-((2R,3R)-3-hydroxy-2-butyloxy)-3-(4-methylsulfonyl)phenylpyridine

Following the procedures described in Example 23, but substituting 2,5-dichloro-3-(4-methylsulfonyl) phenylpyridine from Example 5, Step 2 for 2-chloro-3-(4-methylsulfonyl)phenyl-5-trifluoromethylpyridine, the title compound was obtained as a white solid.

$^1$H NMR (500 MHz, acetone-$d_6$): d 1.12 (d, 3H), 1.26 (d, 3H), 3.16 (s, 3H), 3.78 (d, 1H), 3.85–3.95 (m, 1H), 5.21–5.30 (m, 1H), 7.85 (d, 1H), 7.96–8.01 (m, 4H), 8.17 (d, 1H).

EXAMPLE 25

2-((2R,3S)-3-Hydroxy-2-butyloxy)-3-(4-methylsulfonyl)phenyl-5-trifluoromethylpyridine To a solution of triphenylphosphine (2.5 g) and benzoic acid (1 g) in THF (20 mL) at 0° C. was added 2-((2R,3R)-3-hydroxy-2-butyloxy)-3-(4-methylsulfonyl)phenyl-5-trifluoromethylpyridine (Example 23) followed by the slow addition of a THF solution (5 mL) of diisopropyl azodicarboxylate (2 g). The mixture was warmed to r.t. from 0° C. over 2 h and then saturated sodium carbonate was added and the mixture extracted with ethyl acetate. The organics were filtered through a plug of silica gel and the filtrate was concentrated. The crude benzoate ester was hydrolyzed by stirring in a mixture of methanol/NaOH (1N). After hydrolysis was complete, the mixture was extracted with ethyl acetate, the organics were dried and concentrated. Flash chromatography of the residue (8:2 hexane/ethyl acetate) followed by recrystallization (hexane/ethyl acetate) provided the title compound was obtained as a white solid.

$^1$H NMR (500 MHz, acetone-$d_6$): d 1.15 (d, 3H), 1.32 (d, 3H), 3.16 (s, 3H), 3.84 (d, 1H), 3.90–3.95 (m, 1H), 5.36–5.38 (m, 1H), 8.00–8.03 (m, 4H), 8.10 (d, 1H), 8.50 (d, 1H).

EXAMPLE 26

2-((2S 3S)-3-Hydroxy-2-butyloxy)-3-(4-methylsulfonyl)phenyl-5-trifluoromethylpyridine Following the procedures described in Example 1, but substituting (2S,3S)-2,3-butanediol for ethylene glycol, the title compound was obtained as a white solid, m.p. 115.5–116.5° C.

EXAMPLE 27

2-((2S,3R)-3-Hydroxy-2-butyloxy)-3-(4-methylsulfonyl)phenyl-5-trifluoromethylpyridine To a solution of triphenylphosphine (377 mg) and benzoic acid (176 mg) in THF (5 mL) at −30° C. was added 2-((2S,3S)-3-hydroxy-2-butyloxy)-3-(4-methylsulfonyl) phenyl-5-trifluoromethylpyridine (Example 26) followed by the slow addition of a THF solution (1 mL) of diisopropyl azodicarboxylate (282 mL). The mixture was stirred at 0° C. for 1 h and then saturated sodium carbonate was added and the mixture extracted with ether. The organics were filtered through a plug of silica gel and the filtrate was concentrated. The crude benzoate ester was hydrolyzed by stirring in a mixture of THF/ethanol/water (10 mL, 1:1:1) in the presence of LiOH (3N). After hydrolysis was complete, the mixture was extracted with ethyl acetate, the organics were dried and concentrated. The residual solid was stirred vigorously in ether and the title compound was obtained as a white solid, m.p. 125–125.5° C.

EXAMPLE 28

2-((2R)-1-Hydroxy-2-propyloxy)-3-(4-methylsulfonyl)phenyl-5-trifluoromethylpyridine Step 1: (R)-Methyl 2-(3-(4-methylsulfonyl)phenyl-5-trifluoromethylpyridinyl-2-oxy)propanoate Following the procedures described in Example 1, but substituting (R)-methyl lactate for ethylene glycol, the title compound was obtained as a white solid.

Step 2: 2-((2R)-1-Hydroxy-2-propyloxy)-3-(4-methylsulfonyl)phenyl-5-trifluoromethylpyridine To a solution of the crude ester from Step 1 in THF at r.t was added DIBAL (15 eq). After 1 h, saturated $NH_4Cl$ was added and the mixture extracted with ether. The organics were dried and concentrated. Flash chromatography of the residual material (3:2 hexane/ethyl acetate) provided a mixture of the desired material and the corresponding aldehyde. This mixture was further reduced with sodium borohydride in methanol at room temperature. Following standard workup and flash chromatography (3:2 hexane/ethyl acetate), the title compound was obtained as a white solid.

Elemental Analysis: Calculated: C, 51.20; H, 4.30; N. 3.73 Found: C, 51.01; H, 4.57; N, 3.75

EXAMPLE 29

2-(cis-2-Hydroxycyclopentyloxy)-3-(4-methylsulfonyl)phenyl-5-trifluoromethylpyridine Following the procedures described in Example 1, but substituting cis-1,2-cyclopentanediol for ethylene glycol, the title compound was obtained as a white solid.

Elemental Analysis: Calculated: C, 53.86; H, 4.52; N, 3.49 Found: C, 54.04; H, 4.59; N, 3.50

EXAMPLE 30

2-(trans-2-Hydroxycyclopentyloxy)-3-(4-methylsulfonyl)phenyl-5-trifluoromethylpyridine Following the procedures described in Example 1, but substituting trans-1,2-cyclopentanediol for ethylene glycol, the title compound was obtained as a white solid.

$^1H$ NMR (500 MHz, acetone-$d_6$): d 1.60–1.85 (m, 4H), 1.87–2.00 (m, 1H), 2.17–2.30 (m, 1H), 3.17 (s, 3H), 4.13 (d, 1H), 4.20–4.27 (m, 1H), 5.30–5.3 (m, 1H), 7.95 (d, 2H), 8.04 (d, 2H), 8.12 (d, 1H), 8.58 (d, 1H).

EXAMPLES 31 AND 32

(+)-2-(cis-2-Hydroxy-2-methylcyclopentyloxy)-3-(4-methylsulfonyl)phenyl-5-trifluoromethylpyridine and (−)-2-(cis-2-Hydroxy-2-methylcyclopentyloxy)-3-(4-methylsulfonyl)phenyl-5-trifluoromethylpyridine Step 1: cis-1-Methyl-1,2-cyclopentanediol Following the procedures described in Example 8, Step 1, but substituting 1-methylcyclopentene for 2-ethyl-1-butene, the title compound was obtained in a crude form as an oil and was used without further purification in the next reaction.

Step 2: (+/−)-2-(cis-2-Hydroxy-2-methylcyclopentyloxy)-3-(4-methylsulfonyl)phenyl-5-trifluoromethylpyridine Following the procedures described in Example 1, but substituting cis-1-methyl-1,2-cyclopentanediol from Step 1 for ethylene glycol, the title compound was obtained as a white solid.

Step 3: (+)-2-(cis-2-Hydroxy-2-methylcyclopentyloxy)-3-(4-methylsulfonyl)phenyl-5-trifluoromethylpyridine and (−)-2-(cis-2-Hydroxy-2-methylcyclopentyloxy)-3-(4-methylsulfonyl)phenyl-5-trifluoromethylpyridine A portion (240 mg) of the racemic material obtained in Step 2 was subjected to HPLC using a chiral column (chiralpak AD from DAICEL; 2×25 cm) and an eluant of hexane/isopropanol (83:17) at a flow rate of 9 mL/min (12×20 mg injections). The first compound to be eluted (monitoring at 310 nm) with a retention time of 21.5 min was obtained as a white solid (102 mg) after concentration ($[a]_D$+37°; c=0.65, $CHCl_3$). The second eluting compound (retention time 23.6 min) was obtained as a white solid (101 mg) after concentration ($[a]_D$−28°; c=0.45, $CHCl_3$).

Elemental Analysis: Calculated: C, 54.93; H, 4.85; N, 3.37 Found (+) enantiomer: C, 54.93; H, 5.11; N, 3.39 Found (−) enantiomer: C, 54.62; H, 5.11; N, 3.57

EXAMPLE 33

3-(4-aminosulfonyl)phenyl-2-(cis-2-hydroxy-2-methylcyclopentyloxy)-5-trifluoromethylpyridine Step 1: 3-Bromo-2-chloro-5-trifluoromethylpyridine To a solution of 2-amino-3-bromo-5-trifluoromethylpyridine from Example 1 (15 g) in dioxane/water/12N HCl (75 mL:75 mL:15.5 mL) at 0° C. was added a solution of sodium nitrite (10.54 g). The mixture was stirred for 3 h at r.t. The mixture was poured into an ice bath and then neutralized with 10 N NaOH. The resulting solid was filtered and azeotroped with toluene. The resulting solid and $POCl_3$ (14.5 mL) was heated at 80° C. for 3 h. The mixture was cooled to r.t., poured into an ice bath and then neutralized, first by the addition of 3 N NaOH followed by the addition of saturated sodium carbonate. The resulting mixture was extracted with $CH_2Cl_2$ and the combined organics were washed with brine, dried and concentrated. The title compound was obtained as a volatile liquid that was used without further purification in the next reaction.

Step 2: 3-Bromo-2-(cis-2-hydroxy-2-methylcyclopentyloxy)-5-trifluoromethylpyridine Following the procedures described in Example 31, Step 2, but substituting 3-bromo-2-chloro-5-trifluoromethylpyridine from Step 1 for 2-chloro-3-(4-methylsulfonyl)phenyl-5-trifluoromethyl-pyridine, the title compound was obtained as a white solid.

Step 3: N-t-Butyl-4-bromobenzenesulfonamide

To a solution of 4-bromobenzenesulfonyl chloride (100.2 g) in THF (400 mL) was added t-butylamine (125 mL). An exothermic reaction results with gentle refluxing of the solvent. After 30 min, the bath was removed and the mixture was allowed to warm to r.t. Isopropyl acetate (400 mL) was added and the mixture was washed twice with water. The aqueous phase was back-extracted with ethyl acetate and the combined organics were dried (sodium sulfate) and concentrated to provide the title compound as a solid (112.9 g).

Step 4: 4-t-Butylaminosulfonylbenzene boronic acid

To a solution of N-t-butyl-4-bromobenzenesulfonamide from Step 3 (60.2 g) in THF (700 mL) at 0° C. was added methyl magnesium bromide (75 mL of a 3 M solution in THF). The mixture was stirred at r.t. for 15 min and then cooled to −65° C. n-Butyl lithium (2.35 eq as a solution in hexanes) was added dropwise over 45 min and after addition was complete, the mixture was stirred at −72° C. for 30 min. Triisopropoxyborate (190 mL) was added slowly while the reaction mixture temperature rose to −58° C. Upon completion of the addition, the cold bath was removed and the mixture was warmed to r.t. Concentrated $NH_4Cl$ (500 mL), water (500 mL) and 2N HCl (500 mL) were added successively and then the mixture was adjusted to pH 5–7 with 10 N NaOH. The resulting mixture was stirred at r.t. for 15 h and then isopropyl acetate (700 mL) was added. The aqueous layer was acidified to pH 3 and the phases were separated. The aqueous layer was further extracted with isopropyl acetate/t-butanol (1:1, 600 mL). The combined organics were dried (sodium sulfate) and concentrated. The residue was stirred vigorously in toluene (300 mL) and filtration of the resulting solid provided the title compound (42 g).

Step 5: 4-Aminosulfonylbenzene boronic acid

A solution of 4-t-butylaminosulfonylbenzene boronic acid (500 mg) in TFA (5 mL) was stirred at r.t. for 15 h. The mixture was diluted with ether and the solid material was filtered to provide the title compound.

Step 6: 3-(4-aminosulfonyl)phenyl-2-(cis-2-hydroxy-2-methylcyclopentyloxy)-5-trifluoromethylpyridine A mixture of the bromide (150 mg) from Step 2, 4-aminosulfonylbenzene boronic acid (98 mg), 2M aqueous sodium carbonate (573 mL) and dibromobis (triphenylphosphine)palladium (20 mg) in ethanol/benzene (4.5 mL, 1:1) was heated at reflux for 15 h. The mixture was cooled to r.t., diluted with water and extracted with ether. The organics were concentrated and the residue was subjected to stirred vigorously in ether/hexane for 1 h to provide, after filtration, the title compound (35 mg) as a beige solid.

Elemental Analysis: Calculated: C, 51.92; H, 4.60; N, 6.73 Found: C, 52.10; H, 4.33; N, 6.50

EXAMPLE 34

5-Chloro-2-(cis-2-hydroxy-2-methylcyclopentyloxy)-3-(4-methylsulfonyl) phenylpyridine Following the procedures described in Example 31, Steps 1 and 2, but substituting 2,5-dichloro-3-(4-methylsulfonyl) phenylpyridine from Example 5, Step 2 for 2-chloro-3-(4-methylsulfonyl)phenyl-5-trifluoromethylpyridine, the title compound was obtained as a white solid.

Elemental Analysis: Calculated: C, 56.62; H, 5.28; N, 3.67 Found: C, 56.92; H, 5.53; N. 3.64

EXAMPLE 35

2-(trans-2-Hydroxy-2-methylcyclopentyloxy)-3-(4-methylsulfonyl)phenyl-5-trifluoromethylpyridine Step 1: trans-1-Methyl-1,2-cyclopentanediol To a hot (50° C.) solution of H202 (1.3 mL of a 13 M solution in water), acetic acid (6.1 mL) and tungsten(VI) oxide (20 mg) was added slowly 1-methylcyclopentene (1 g). The mixture was stirred at 50° C. for 15 h and then the acetic acid was removed in vacuo. 2 M NaOH (10 mL) was added and the mixture was refluxed for 90 min. The mixture was cooled to r.t., the aqueous phase was saturated with NaCl solid and then extracted 5 times with ethyl acetate. The combined organics were dried, filtered through a pad of silica gel, eluting with ethyl acetate/ethanol. The filtrate was concentrated and the crude brownish paste, containing the title compound, was used without further purification in the next step.

Step 2: 2-(trans-2-Hydroxy-2-methylcyclopentyloxy)-3-(4-methylsulfonyl)phenyl-5-trifluoromethylpyridine Following the procedures described in Example 1, but substituting trans-1-methyl-1,2-cyclopentanediol from Step 1 for ethylene glycol, the title compound was obtained as a white solid.

Elemental Analysis: Calculated: C, 54.93; H, 4.85; N, 3.37 Found: C, 54.73; H, 4.86; N, 3.45

EXAMPLE 36

2-(cis-2-Hydroxy-2-ethylcyclopentyloxy)-3-(4-methylsulfonyl)phenyl-5-trifluoromethylpyridine Step 1: cis-1-Ethyl-1i2-cyclopentanediol To a solution of cyclopentanone (17.7 mL) in THF (400 mL) at 0° C. was added ethyl magnesium bromide (100 mL of a 3M solution in THF) and the resulting mixture was stirred at r.t. for 2 h. Saturated $NH_4Cl$ was added and the mixture extracted with ether. The organics were combined and concentrated. A portion of the material so produced (10 g) was treated with 85% H3PO4 (catalytic amount) and heated to 115° C. The desired 1-ethylcyclopentene (3.4 g) was distilled off as it was formed. Dihydroxylation was accomplished by following the procedures described in Example 8, Step 1, but substituting 1-ethylcyclopentene for 2-ethyl-1-butene. In such a way the title compound was obtained in a crude form as an oil and was used without further purification in the next reaction.

Step 2: 2-(cis-2-Hydroxy-2-ethylcyclopentyloxy2W)-3-(4-methylsulfonyl)phenyl-5-trifluoromethyl-pyridine Following the procedures described in Example 1, but substituting cis-1-ethyl-1,2-cyclopentanediol from Step 1 for ethylene glycol, the title compound was obtained as a white solid.

Elemental Analysis: Calculated: C, 55.94; H, 5.16; N, 3.26 Found: C, 56.13; H, 5.25; N, 3.28

EXAMPLE 37

2-(cis-2-Hydroxyy-2-methyl cyclohexyloxy)-3-(4-methylsulfonyl )phenyl-5-trifluoromethylpyridine Step 1: cis- 1-Methyl- 2-cyclohexanediol Following the procedures described in Example 8, Step 1, but substituting 1-methylcyclohexene for 2-ethyl-1-butene, the title compound was obtained in a crude form as an oil and was used without further purification in the next reaction.

Step 2: 2-(cis-2-Hydroxy-2-methylcyclohexyloxy)-3-(4-methylsulfonyl)phenyl-5-trifluoromethylpyridine Following the procedures described in Example 1, but substituting cis-1-methyl-1,2-cyclohexanediol from Step 1 for ethylene glycol, the title compound was obtained as a white solid, m.p. 93.5-95° C.

EXAMPLE 38

2-((3S)-3-Hydroxy- 1-butyloxy)-3-(4-methylsulfonyl)phenyl-5-trifluoromethylpyridine To a solution of (S)-1,3-butanediol (807 mg) in DMF (10 mL) at 0° C. was added potassium t-butoxide (7.2 mL of a 1M solution in THF). After 1 h, the mixture was cooled to −20° C. and then 2-chloro-3-(4-methylsulfonyl)phenyl-5-trifluoromethylpyridine (1 g) was added as a solid. The resulting mixture was stirred for 24 h, warming to r.t. To the mixture was added saturated NH4Cl and the mixture was extracted with ethyl acetate. The organics were dried ($MgSO_4$) and concentrated. Flash chromatography (1:1 hexane/ethyl acetate) provided the title compound as a white solid (323 mg).

$^1H$ NMR (300 MHz, acetone-$d_6$): d 1.15 (d, 3H), 1.75–2.00 (m, 2H), 3.15 (s, 3H), 3.65 (d, 1H), 3.85–4.00 (m, 1H), 4.60 (dd, 2H), 7.95 (d, 2H), 8.03 (d, 8.10 (d, 1H), 8.57 (d, 1H).

EXAMPLE 39

2-((3R)-3-Hydroxy- 1-butyloxy)-3-(4-methylsulfonyl)phenyl-5-trifluoromethylpyridine Step 1: (R)-1-t-Butyldiphenylsiloxy-3-butanol A mixture of (R)-1,3-butanediol (2 g), triethylamine (4 mL) and t-butyldiphenylchlorosilane (6.7 g) in $CH_2Cl_2$ (80 mL) was stirred at r.t. for 15 h. Saturated $NH_4Cl$ was added and the mixture was extracted with ethyl acetate. The combined organics were dried ($MgSO_4$) and concentrated. Flash chromatography of the residue (9:1 hexane/ethyl acetate) provided the title compound as an oil.

Step 2: 2-((3R)-3-Acetoxy- 1-butyloxy)-3-(4-methylsulfonyl)phenyl-5-trifluoromethylpyridine and 2-((2R)-4-Acetoxy-2-butyloxy)-3-(4-methylsulfonyl)phenyl-5-trifluoromethylpyridine Following the procedures described in Example 38, but substituting (R)-1-t-butyldiphenylsiloxy-3-butanol from Step 1 for (S)-1,3-butanediol, followed by treating the mixture of regioisomeric diols with acetic anhydride in pyridine at r.t. for 1 h, the title compounds were obtained. Upon flash chromatography (9:1 hexane/ethyl acetate) of the crude acetates, which contained both regioisomers, the first compound to be eluted was 2-((3R)-3-acetoxy-1-butyloxy)-3-(4-methylsulfonyl)phenyl-5-trifluoromethylpyridine. Recrystallization (hexane/ethyl acetate) of column fractions that were enriched in this regioisomer provided a sample of pure material (500 mg). Column fractions that were enriched in the alternative regioisomer (200 mg), 2-((2R)-4-acetoxy-2-butyloxy)-3-(4-methylsulfonyl)phenyl-5-trifluoromethylpyridine, were used in Example 41.

Step 3: 2-((3R)-3-Hydroxy-1-butyloxy)-3-(4-methylsulfonyl)phenyl-5-trifluoromethylpyridine A solution of 2-((3R)-3-acetoxy-1-butyloxy)-3-(4-methylsulfonyl)phenyl-5-trifluoromethylpyridine (500 mg) from Step 2 and 1 N NaOH (3 mL) in methanol (10 mL) was stirred at r.t. for 15 h. 1 N HCl (3 mL) was added and the organics were removed in vacuo. The residual aqueous phase was extracted with ethyl acetate and the organics were washed with brine, dried ($MgSO_4$) and concentrated. The title compound was obtained as a white solid.

$^1H$ NMR (500 MHz, acetone-$d_6$): d 1.15 (d, 3H), 1.77–1.96 (m, 2H), 3.19 (s, 3H), 3.67 (d, 1H), 3.88–3.98 (m, 1H), 4.60 (dd, 2H), 7.96 (d, 2H), 8.02 (d, 8.10 (d, 1H), 8.57 (d, 1H).

EXAMPLE 40

2-(3-Hydroxy-3-methyl-1-butyloxy)-3-(4-methylsulfonyl)phenyl-5-trifluoromethylpyridine Following the procedures described in Example 1, but substituting 4-methyl-1,3-butanediol for ethylene glycol, the title compound was obtained as a white solid.

Elemental Analysis: Calculated: C, 53.59; H, 5.0; N, 3.47 Found: C, 53.35; H, 5.19; N, 3.42

EXAMPLE 41

2-((2R)-4-Hydroxy-2-butyloxy)-3-(4-methylsulfonyl)phenyl-5- trifluoromethylpyridine Column fractions that were enriched in 2-((2R)-4-acetoxy-2-butyloxy)-3-(4-methylsulfonyl)phenyl-5-trifluoromethylpyridine (from Example 39, Step 2) were hydrolyzed following the procedures described in Example 39, Step 3. Flash chromatography of the residue (1:1 hexane/ethyl acetate) provided the title compound as a solid.

$^1H$ NMR (500 MHz, acetone-$d_6$): d 1.37 (d, 3H), 1.76–1.89 (m, 1H), 1.89–2.00 (m, 1H), 3.18 (s, 3H), 3.55–3.60 (m, 1H), 3.60–3.68 (m, 3H), 7.95 (d, 2H), (d, 2H), 8.09 (d, 1H), 8.56 (d, 1H).

EXAMPLE 42

2-(2-Hydroxy)thioethoxy-3-(4-methylsulfonyl)phenyl-5-trifluoromethylpyridine

A mixture of 2-chloro-3-(4-methylsulfonyl)phenyl-5-trifluoromethylpyridine (200 mg), 2-mercaptoethanol (84 mL) and triethylamine (416 mL) in DMF (3 mL) was stirred at r.t. for 15 h. Saturated sodium bicarbonate was added and the mixture extracted with ethyl acetate. The organics were washed with brine, dried ($MgSO_4$) and concentrated. The residual solid was stirred vigorously in ether and the title compound was obtained as a white solid, m.p. 156–158.5° C.

EXAMPLE 43

2-(2-Hydroxy-2-methyl- 1-thiopropyloxy)-3-(4-methylsulfonyl)phenyl-5-trifluoromethylpyridine Step 1: 3-Hydroxy-3-methylpropanethiol To a solution of methyl thioglycolate (5 mL) in THF (90 mL) at r.t. was rapidly added methyl magnesium bromide (50 mL of a 3 M solution in THF). The mixture was stirred for 15 h at a bath temperature of 100° C. The mixture was cooled to r.t. and then poured slowly into a stirred solution of saturated $NH_4Cl$ (150 mL). Saturated NaCl was added and the mixture was extracted 5 times with ether. The combined organics were dried and concentrated to provide the title compound (3 g) that was used without further purification in the next reaction.

Step 2: 2-(2-Hydroxy-2-methyl-1-thiopropyloxy)-3-(4-methylsulfonyl)phenyl-5-trifluoromethylpyridine A mixture of 2-chloro-3-(4-methylsulfonyl)phenyl-5-trifluoromethylpyridine (336 mg), 3-hydroxy-3-methylpropanethiol (127 mg) and potassium carbonate (excess) in DMSO (10 mL) was stirred at r.t. for 2 h. Saturated $NH_4Cl$ was added and the mixture extracted with ethyl acetate. The organics were washed with brine, dried ($MgSO_4$) and concentrated. Flash chromatography of the residual material, followed by stirring the partially purified material vigorously in ether, provided the title compound as a pale yellow solid (324 mg).

Elemental Analysis: Calculated: C, 50.36; H. 4.47; N, 3.45 Found: C, 50.17; H, 4.55; N, 3.45

EXAMPLE 44

5-Chloro-2-(2-Hydroxy-2-methyl-1-thiopropyloxy)-3-(4-methylsulfonyl)phenylpyridine Following the procedures described in Example 43, but substituting 2,5-dichloro-3-(4-methylsulfonyl)phenylpyridine for 2-chloro-3-(4-methylsulfonyl)phenyl-5-trifluoromethylpyridine, the title compound was obtained as a white solid.

Elemental Analysis: Calculated: C, 51.67; H, 4.88; N, 3.77 Found: C, 51.59; H, 4.93; N, 3.85

EXAMPLES 45 AND 46

(+)-2-(2-Hydroxy-2-methyl- 1-thiobutyloxy)-3-(4-methylsulfonyl)phenyl-5-trifluoromethylpyridin and (−)-2-(2-Hydroxy-2-methyl-1-thiobutyloxy)-3-(4-methylsulfonyl)phenyl-5-trifluoromethylpyridine Step 1: Triphenylsilyl(2-hydroxy-2-methylbutyl)sulfide Following the procedures described in Example 47, Step 1, but substituting 2-methyl-1-butene for 2-ethyl-1-butene, the title compound was obtained as an impure oil that was used without further purification in the next step.

Step 2: (+/−)-2-(2-Hydroxy-2-methyl-1-thiobutyloxy)-3-(4-methylsulfonyl)phenyl-5-trifluoromethylpyridine Following the procedures described in Example 47, Step 2, but substituting triphenylsilyl(2-hydroxy-2-methylbutyl) sulfide from Step 1 for triphenylsilyl(2-ethyl-2-hydroxybutyl)sulfide, the title compound was obtained as a white solid.

Step 3: (+)-2-(2-Hydroxy-2-methyl- 1-thiobutyloxy)-3-(4-methylsulfonyl)phenyl-5-trifluoromethylpyridine and (−)-2-(2- Hydroxy-2-methyl-1-thiobutyloxy)-3-(4-methylsulfonyl)phenyl-5-trifluoromethylpyridine A portion (500 mg) of the racemic material obtained in Step 2 was subjected to HPLC using a chiral column (chiralpak AD from DAICEL; 2×25 cm) and an eluant of hexane/isopropanol (78:22) at a flow rate of 9 mL/min (10×50 mg injections). The first compound to be eluted (monitoring at 334 nm) with a retention time of 24.8 min was obtained as a white solid (170 mg) after concentration ($[a]_D$+15°; c=1, $CHCl_3$). The second eluting compound (retention time 26.6 min) was obtained as a white solid (170 mg) after concentration ($[a]_D$−12°; c=1.2, $CHCl_3$).

Elemental Analysis: Calculated: C, 51.54; H, 4.81; N, 3.34 Found (+) enantiomer: C, 51.25; H, 4.70; N. 3.34 Found (−) enantiomer: C, 51.33; H, 4.71; N. 3.18

EXAMPLE 47

2-(2-Ethyl-2-hydroxy-1-thiobutyloxy)-3-(4-methylsulfonyl)phenyl-5-trifluoromethylpyridine Step 1: Triphenylsilyl(2-ethyl-2-hydroxybutyl)sulfide To a solution of 2-ethyl-1-butene (2 g) in THF (25 mL) at 0° C. was added mCPBA (6 g of 80% material) and the resulting mixture was stirred at r.t. for 30 min. Calcium hydroxide (3 g) was added and after 15 min, the mixture was filtered and the filtrate concentrated. A mixture of the crude epoxide, triethylamine (5 mL) and triphenylsilanethiol (6 g) in THF (50 mL) was heated at reflux for 24 h and then stirred at r.t. for 7 days. Saturated $NH_4Cl$ was added and the mixture was extracted with ethyl acetate. The organics were concentrated and then hexane/ether were added. After vigorous stirring, the mixture was filtered and the filtrate was concentrated to yield the title compound as an impure oil that was used as such in the next step.

Step 2: 2-(2-Ethyl-2-hydroxy-1-thiobutyloxy)-3-(4-methylsulfonyl)phenyl-5-trifluoromethylpyridine To a solution of 2-chloro-3-(4-methylsulfonyl)phenyl-5-trifluoromethylpyridine (Example 1, Step 4) (500 mg) and the crude sulfide from Step 1 (~1 g) in THF (20 mL) at r.t. was added TBAF (3 mL of a 1 M solution in THF). After 1 h, water was added and the mixture was extracted with ether. The organics were concentrated and the residue subjected to flash chromatography (7:3 hexane/ethyl acetate). The resulting solid was stirred vigorously in pentane/ether and the title compound was obtained as a white solid.

Elemental Analysis: Calculated: C, 52.73; H, 5.08; N, 3.14 Found: C, 52.64; H, 5.12; N, 3.23

EXAMPLE 48

5-Chloro-2-(2-ethyl-2-hydroxy-1-thiobutyloxy)-3-(4-methylsulfonyl)phenylpyridine Following the procedures described in Example 47, but substituting 2,5-dichloro-3-(4-methylsulfonyl)phenylpyridine for 2-chloro-3-(4-methylsulfonyl)phenyl-5-trifluoromethylpyridine, the title compound was obtained as a white solid.

Elemental Analysis: Calculated: C, 54.06; H, 5.54; N. 3.50 Found: C, 53.45; H, 5.47; N, 3.48

EXAMPLE 49

2-(1-Hydroxycyclopentyl)thiomethoxy-3-(4-methylsulfonyl)phenyl-5-trifluoromethylpyridine Following the procedures described in Example 47, but substituting methylenecyclopentane for 2-ethyl-1-butene, the title compound was obtained as a white solid.

Elemental Analysis: Calculated: C, 52.89; H, 4.67; N, 3.25 Found: C, 52.89; H, 4.72; N. 3.16

EXAMPLE 50

2-(3-Hydroxy-2-thiopropyloxy)-3-(4-methylsulfonyl)phenyl-5-trifluoromethylpyridine A mixture of 2,5-dichloro-3-(4-methylsulfonyl)phenylpyridine (336 mg), thiolactic acid (135 mL), and $Cs_2CO_3$ (1 g) in THF (10 mL) was stirred at r.t. for 15 h. Saturated $NH_4Cl$ was added and the mixture was extracted with ether. The organics were concentrated and the residue was treated with diazomethane to provide the methyl ester. The ester was dissolved in THF and treated with DIBAL at r.t. After reduction was complete, water was added and the mixture extracted with ethyl acetate. The organics were dried and concentrated. The residual material was subjected to flash chromatography (1:1 hexane/ethyl acetate) and then stirred vigorously in ether to provide the title compound (88 mg) as a pale yellow solid.

Elemental Analysis: Calculated: C, 49.10; H, 4.12; N, 3.58 Found: C, 48.75; H, 4.16; N, 3.58

EXAMPLE 51

5-Chloro-2-((Z)-3-Hydroxy-3-methyl-1-butenyl)-3-(4-methylsulfonyl)phenylpyridine Step 1: 5-Chloro-2-(3-Hydroxy-3-methyl- 1-butynyl)-3-(4-methylsulfonyl)phenylpyridine A mixture of 2,5-dichloro-3-(4-methylsulfonyl)phenylpyridine (3 g), 2-methyl-3-butyn-2-ol (1.85 g), triethylamine (5.5 mL), dibromobistriphenylphosphine palladium (790 mg) and CuI (100 mg) in MeCN (100 mL) was heated at reflux for 1 h. The mixture was cooled to r.t. then filtered through a pad of Celite. The filtrate was concentrated, water was added and the mixture extracted with ethyl acetate. The organic phase was extracted several times with 6 N HCl and then the aqueous phases were neutralized with 10 N NaOH and re-extracted with ethyl acetate. The latter organics were dried ($MgSO_4$) and concentrated. Flash chromatography (1:1 hexane/ethyl acetate) of the residue followed by recrystallization (hexane/ethyl acetate) provided the title compound as a solid (3 g).

Step 2: 5-Chloro-2-((Z)-3-Hydroxy-3-methyl-1-butenyl)-3-(4-methylsulfonyl)phenylpyridine A mixture of the acetylene from Step 1 (2.75 g) and Lindlar's catalyst (500 mg) in THF (100 mL) was shaken under an atmosphere of hydrogen (15 psi) for 90 min after which time, approximately 50% of the starting material was consumed. The mixture was filtered through a pad of Celite and the filtrate was concentrated. Flash chromatography of the residue (1:1 hexane/ethyl acetate) provided the title compound as a white solid (900 mg).

Elemental Analysis: Calculated: C, 58.17; N, 3.96; H, 5.21 Found: C, 58.03; N, 3.98; H, 5.16

What is claimed is:

1. A compound of formula I

I

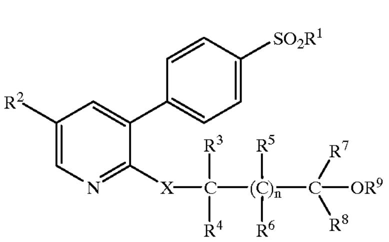

or a pharmaceutically acceptable salt thereof, wherein:

X is selected from the group consisting of:
(a) O,
(b) S and
(c) a bond, n is 0 or 1, $R^1$ is selected from the group consisting of.
(a) $CH_3$,
(b) $NH_2$ and
(c) $NHC(O)CF_3$, $R^2$ is selected from the group consisting of:
(a) halo,
(b) $C_{1-6}$alkoxy,
(c) $C_{1-6}$alkylthio,
(d) CN,
(e) $C_{1-6}$alkyl,
(f) $C_{1-6}$fluoroalkyl,
(g) $N_3$,
(h) —$CO_2R^{10}$,
(i) hydroxy,
(j) —$C(R^{11})(R^{12})$—OH,
(k) —$C_{1-6}$alkyl-$CO_2$-$R^{13}$,
(1) $C_{1-6}$fluoroalkoxy,
(m) $NO_2$,
(n) $NR^{14}R^{15}$ and
(o) $NHCOR^{16}$, and $R^3$ to $R^{16}$ are independently selected from the group consisting of:
(a) hydrogen and
(b) $C_{1-6}$alkyl, or $R^3$ and $R^7$, or $R^7$ and $R^8$ together with the atoms to which they are attached form a carbocyclic ring of 3, 4, 5, 6 or 7 atoms, or $R^3$ and $R^5$ are joined to form a bond.

2. A compound according to claim 1 wherein X is a bond.

3. A compound according to claim 1 wherein $R^1$ is $CH_3$.

4. A compound according to claim 1 wherein $R^2$ is selected from the group consisting of:
(a) halo,
(b) $C_{1-4}$alkoxy,
(c) $C_{1-4}$alkylthio,
(d) CN,
(e) $C_{1-4}$alkyl,
(f) $C_{1-4}$fluoroalkyl,
(g) —$CO_2R^{10}$ and
(h) hydroxy.

5. A compound of formula I

I

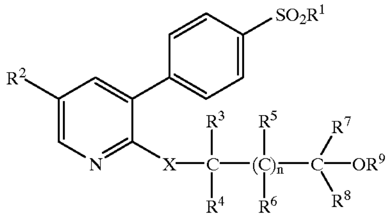

or pharmaceutically acceptable salt thereof, wherein:

X is O, n is 0 or 1, $R^1$ is selected from the group consisting of:
(a) $CH_3$,
(b) $NH_2$ and
(c) $NHC(O)CF_3$, $R^2$ is selected from the group consisting of:
(a) halo,
(b) $C_{1-6}$alkoxy,
(c) $C_{1-6}$alkylthio,
(d) CN,
(e) $C_{1-6}$alkyl,
(f) $C_{1-6}$fluoroalkyl,
(g) $N_3$,
(h) —$CO_2R^{10}$,
(i) hydroxy,
(j) —$C(R^{11})(R^{12})$—OH,
(k) —$C_{1-6}$alkyl-$CO_2$-$R^{13}$,
(l) $C_{1-6}$fluoroalkoxy,
(m) $NO_2$,
(n) $NR^{14}R^{15}$and
(o) $NHCOR^{16}$, and $R^3$ to $R^{16}$ are independently selected from the group consisting of:
(a) hydrogen and
(b) $C_{1-6}$alkyl, or $R^3$ and $R^7$, or $R^7$ and $R^8$ together with the atoms to which they are attached form a carbocyclic ring of 3, 4, 5, 6 or 7 atoms, or $R^3$ and $R^5$ are joined to form a bond.

6. A compound of formula I

I

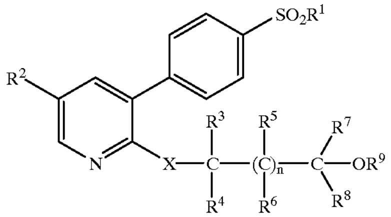

or pharmaceutically acceptable salt thereof, wherein:

X is S, n is 0 or 1, $R^1$ is selected from the group consisting of:
(a) $CH_3$,
(b) $NH_2$ and
(c) $NHC(O)CF_3$, $R^2$ is selected from the group consisting of:
(a) halo,
(b) $C_{1-6}$alkoxy, (c) $C_{1-6}$alkylthio,
(d) CN,
(e) $C_{1-6}$alkyl,
(f) $C_{1-6}$fluoroalkyl,
(g) $N_3$,
(h) $—CO_2R^{10}$,
(i) hydroxy,
(j) $—C(R^{11})(R^{12})—OH$,
(k) $—C_{1-6}alkyl—CO_2-R^{13}$,
(l) $C_{1-6}$fluoroalkoxy,
(m) $NO_2$,
(n) $NR^{14}R^{15}$ and
(o) $NHCOR^{16}$, and $R^3$ to $R^{16}$ are independently selected from the group consisting of:
(a) hydrogen and
(b) $C_{1-6}$alkyl, or $R^3$ and $R^7$, or $R^7$ and $R^8$ together with the atoms to which they are attached form a carbocyclic ring of 3, 4, 5, 6 or 7 atoms, or $R^3$ and $R^5$ are joined to form a bond.

7. A compound according to claim 1 wherein $R^2$ is selected from the group consisting of:
(a) halo,
(b) $C_{1-4}$alkoxy,
(c) $C_{1-4}$alkylthio,
(d) CN,
(e) $C_{1-4}$alkyl and
(f) $C_{1-4}$fluoroalkyl.

8. A compound according to claim 1 wherein $R^2$ is halo or $C_{1-6}$fluoroalkyl.

9. A compound according to claim 1 wherein n is 0.

10. A compound according to claim 1 wherein

X is selected from the group consisting of:
(a) O,
(b) S and
(c) a bond, $R^1$ is selected from the group consisting of:
(a) $CH_3$ and
(b) $NH_2$, and $R^2$ is selected from the group halo or $C_{1-6}$fluoroalkyl.

11. A compound according to claim 1 of the formula:

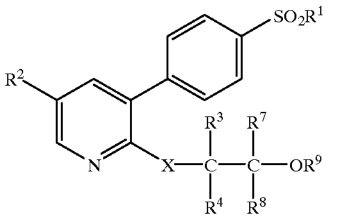

wherein:

X is selected from the group consisting of:
(a) O,
(b) S and
(c) a bond, $R^1$ is selected from the group consisting of:
(a) $CH_3$ and
(b) $NH_2$, $R^2$ is selected from the group consisting of:
(a) halo,
(b) $C_{1-4}$alkoxy,
(c) $C_{1-4}$alkylthio,
(d) CN,
(e) $C_{1-4}$alkyl,
(f) $C_{1-4}$fluoroalkyl,
(g) $—CO_2R^{10}$ and
(h) hydroxy, and $R^3$, $R^4$, $R^7$, $R^8$ and $R^9$ are independently selected from the group consisting of:
(a) hydrogen and
(b) $C_{1-6}$alkyl, or $R^3$ and $R^7$, or $R^7$ and $R^8$ together with the atoms to which they are attached form a carbocyclic ring of 3, 4, 5, 6 or 7 atoms.

12. A compound according to claim 9 wherein:

X is selected from the group consisting of:
(a) O,
(b) S and
(c) a bond, $R^1$ is selected from the group consisting of:
(a) $CH_3$ and
(b) $NH_2$, $R^2$ is halo or $C_{1-6}$fluoroalkyl, and $R^3$, $R^4$, $R^7$, $R^8$ and $R^9$ are independently selected from the group consisting of:
(a) hydrogen and
(b) $C_{1-6}$alkyl, or $R^3$ and $R^7$, or $R^7$ and $R^8$ together with the atoms to which they are attached form a carbocyclic ring of 3, 4, 5, 6 or 7 atoms.

13. A compound according to claim 12 wherein:

X is selected from the group consisting of:
(a) O,
(b) S and
(c) a bond, $R^1$ is selected from the group consisting of:
(a) $CH_3$ and
(b) $NH_2$, $R^2$ is halo or $C_{1-6}$fluoroalkyl, and $R^3$, $R^4$, $R^7$, $R^8$ and $R^9$ are independently selected from the group consisting of:
(a) hydrogen and
(b) $C_{1-6}$alkyl.

14. A compound selected from the group consisting of:

(1) 2-(2-Hydroxy)ethoxy-3-(4-methylsulfonyl)phenyl-5-trifluoromethylpyridine,
(2) 2-(2-Methoxy)ethoxy-3-(4-methylsulfonyl)phenyl-5-trifluoromethylpyridine,
(3) 2-(2-Hydroxy-1-propyloxy)-3-(4-methylsulfonyl)phenyl-5-trifluoromethylpyridine,
(4) 2-(2-Hydroxy-2-methyl-1-propyloxy)-3-(4-methylsulfonyl)phenyl-5-trifluoromethylpyridine
(5) 5-Chloro-2-(2-hydroxy-2-methyl-1-propyloxy)-3-(4-methylsulfonyl)phenylpyridine,
(6) 2-(2-Methoxy-2-methyl-1-propyloxy)-3-(4-methylsulfonyl)phenyl-5-trifluoromethylpyridine
(7) 2-(2-Hydroxy-2-methyl-1-butyloxy)-3-(4-methylsulfonyl)phenyl-5-trifluoromethylpyridine
(8) 2-(2-Hydroxy-2-ethyl-1-butyloxy)-3-(4-methylsulfonyl)phenyl-5-trifluoromethylpyridine
(9) 5-Chloro-2-(2-hydroxy-2-ethyl-1-butyloxy)-3-(4-methylsulfonyl)phenylpyridine,
(10) 2-(2-Hydroxy-2-phenyl-1-propyloxy)-3-(4-methylsulfonyl)phenyl-5-trifluoromethylpyridine
(11) 2-(1-Hydroxycyclopropyl)methoxy-3-(4-methylsulfonyl)phenyl-5-trifluoromethylpyridine,
(12) 2-(1-Hydroxycyclobutyl)methoxy-3-(4-methylsulfonyl)phenyl-5-trifluoromethylpyridine,

(13) 2-(1-Hydroxycyclopentyl)methoxy-3-(4-methylsulfonyl)phenyl-5-trifluoromethylpyridine,

(14) 5-Chloro-2-(1-hydroxycyclopentyl)methoxy-3-(4-methylsulfonyl)phenylpyridine,

(15) 2-(1-Hydroxycyclohexyl)methoxy-3-(4-methylsulfonyl)phenyl-5-trifluoromethylpyridine,

(16) 2-((2S)-3-Hydroxy-3-methyl-2-butyloxy)-3-(4-methylsulfonyl)phenyl-5-trifluoromethylpyridine

(17) 2-((2R)-3-Hydroxy-3-methyl-2-butyloxy)-3-(4-methylsulfonyl)phenyl-5-trifluoromethylpyridine,

(18) 5-Chloro-2-((2R)-3-Hydroxy-3-methyl-2-butyloxy)-3-(4-methylsulfonyl)phenylpyridine,

(19) 2-(4-Hydroxy-4-methyl-3-pentyloxy)-3-(4-methylsulfonyl)phenyl-5-trifluoromethylpyridine

(20) 2-((2S)-3-Ethyl-3-hydroxy-2-pentyloxy)-3-(4-methylsulfonyl)phenyl-5-trifluoromethylpyridine,

(21) 2-((2R)-3-Ethyl-3-hydroxy-2-pentyloxy)-3-(4-methylsulfonyl)phenyl-5-trifluoromethylpyridine,

(22) 2-(1-(1-Hydroxycyclopentyl)ethoxy)-3-(4-methylsulfonyl)phenyl-5-trifluoromethylpyridine,

(23) 2-((2R,3R)-3-Hydroxy-2-butyloxy)-3-(4-methylsulfonyl)phenyl-5-trifluoromethylpyridine,

(24) 5-Chloro-2-((2R,3R)-3-hydroxy-2-butyloxy)-3-(4-methylsulfonyl)phenylpyridine,

(25) 2-((2R,3S)-3-Hydroxy-2-butyloxy)-3-(4-methylsulfonyl)phenyl-5-trifluoromethylpyridine,

(26) 2-((2S,3S)-3-Hydroxy-2-butyloxy)-3-(4-methylsulfonyl)phenyl-5-trifluoromethylpyridine,

(27) 2-((2S,3R)-3-Hydroxy-2-butyloxy)-3-(4-methylsulfonyl)phenyl-5-trifluoromethylpyridine,

(28) 2-((2R)-1-Hydroxy-2-propyloxy)-3-(4-methylsulfonyl)phenyl-5-trifluoromethylpyridine,

(29) 2-(cis-2-Hydroxycyclopentyloxy)-3-(4-methylsulfonyl)phenyl-5-trifluoromethylpyridine,

(30) 2-(trans-2-Hydroxycyclopentyloxy)-3-(4-methylsulfonyl)phenyl-5-trifluoromethylpyridine,

(31) (+)-2-(cis-2-Hydroxy-2-methylcyclopentyloxy)-3-(4-methylsulfonyl)phenyl-5-trifluoromethylpyridine,

(32) (−)-2-(cis-2-Hydroxy-2-methylcyclopentyloxy)-3-(4-methylsulfonyl)phenyl-5-trifluoromethylpyridine,

(33) 3-(4-aminosulfonyl)phenyl-2-(cis-2-hydroxy-2-methylcyclopentyloxy)-5-trifluoromethylpyridine,

(34) 5-Chloro-2-(cis-2-hydroxy-2-methylcyclopentyloxy)-3-(4-methylsulfonyl)phenylpyridine,

(35) 2-(trans-2-Hydroxy-2-methylcyclopentyloxy)-3-(4-methylsulfonyl)phenyl-5-trifluoromethylpyridine,

(36) 2-(cis-2-Hydroxy-2-ethylcyclopentyloxy)-3-(4-methylsulfonyl)phenyl-5-trifluoromethylpyridine,

(37) 2-(cis-2-Hydroxy-2-methylcyclohexyloxy)-3-(4-methylsulfonyl)phenyl-5-trifluoromethylpyridine,

(38) 2-((3S)-3-Hydroxy-1-butyloxy)-3-(4-methylsulfonyl)phenyl-5-trifluoromethylpyridine,

(39) 2-((3R)-3-Hydroxy-1-butyloxy)-3-(4-methylsulfonyl)phenyl-5-trifluoromethylpyridine,

(40) 2-(3-Hydroxy-3-methyl-1-butyloxy)-3-(4-methylsulfonyl)phenyl-5-trifluoromethylpyridine,

(41) 2-((2R)-4-Hydroxy-2-butyloxy)-3-(4-methylsulfonyl)phenyl-5-trifluoromethylpyridine,

(42) 2-(2-Hydroxy)thioethoxy-3-(4-methylsulfonyl)phenyl-5-trifluoromethylpyridine,

(43) 2-(2-Hydroxy-2-methyl-1-thiopropyloxy)-3-(4-methylsulfonyl)phenyl-5-trifluoromethylpyridine,

(44) 5-Chloro-2-(2-Hydroxy-2-methyl-1-thiopropyloxy)-3-(4-methylsulfonyl)phenylpyridine,

(45) (+)-2-(2-Hydroxy-2-methyl-1-thiobutyloxy)-3-(4-methylsulfonyl)phenyl-5-trifluoromethylpyridine,

(46) (−)-2-(2-Hydroxy-2-methyl-1-thiobutyloxy)-3-(4-methylsulfonyl)phenyl-5-trifluoromethylpyridine,

(47) 2-(2-Ethyl-2-hydroxy-1-thiobutyloxy)-3-(4-methylsulfonyl)phenyl-5-trifluoromethylpyridine,

(48) 5-Chloro-2-(2-ethyl-2-hydroxy-1-thiobutyloxy)-3-(4-methylsulfonyl)phenylpyridine,

(49) 2-(1-Hydroxycyclopentyl)thiomethoxy-3-(4-methylsulfonyl)phenyl-5-trifluoromethylpyridine,

(50) 2-(3-Hydroxy-2-thiopropyloxy)-3-(4-methylsulfonyl)phenyl-5-trifluoromethylpyridine, and

(51) 5-Chloro-2-((Z)-3-Hydroxy-3-methyl-1-butenyl)-3-(4-methylsulfonyl)phenylpyridine.

15. A method of treating an inflammatory disease susceptible to treatment with a non-steroidal anti-inflammatory agent comprising administering to a patient in need of such treatment a non-toxic therapeutically effective amount of a compound according to claim 1 and a pharmaceutically acceptable carrier.

16. A method of treating cyclooxygenase mediated diseases advantageously treated by an active agent that selectively inhibits COX-2 in preference to COX- 1 comprising administering to a patient in need of such treatment a non-toxic therapeutically effective amount of a compound according to claim 1.

17. A pharmaceutical composition comprising a compound of claim 1 in combination with a pharmaceutically acceptable carrier.

* * * * *